(12) United States Patent  
Li et al.

(10) Patent No.: US 8,124,032 B2  
(45) Date of Patent: Feb. 28, 2012

(54) MICROFLUIDIC DEVICE AND METHOD OF USING SAME

(75) Inventors: Paul Chi Hang Li, Coquitlam (CA); Xing Yue Peng, Burnaby (CA)

(73) Assignee: Simon Fraser University, Burnaby, British Columbia (CA)

( * ) Notice: Subject to any disclaimer, the term of this patent is extended or adjusted under 35 U.S.C. 154(b) by 1208 days.

(21) Appl. No.: 11/572,134

(22) PCT Filed: Jul. 15, 2005

(86) PCT No.: PCT/CA2005/001117  
§ 371 (c)(1),  
(2), (4) Date: Aug. 30, 2007

(87) PCT Pub. No.: WO2006/007701  
PCT Pub. Date: Jan. 26, 2006

(65) Prior Publication Data  
US 2008/0138848 A1    Jun. 12, 2008

Related U.S. Application Data

(60) Provisional application No. 60/588,317, filed on Jul. 16, 2004.

(51) Int. Cl.  
*B01D 21/00* (2006.01)  
*G01N 21/00* (2006.01)  
*G01N 15/06* (2006.01)  
*G01N 33/48* (2006.01)  
*C12M 3/00* (2006.01)  
*G01N 21/64* (2006.01)  
*B01D 11/04* (2006.01)  
*C12M 1/34* (2006.01)  
*C12N 1/00* (2006.01)  
*G01N 23/00* (2006.01)

(52) U.S. Cl. ...... 422/527; 422/68.1; 422/81; 422/82.05; 422/82.08; 422/82.09; 422/255; 435/287.2; 435/288.5; 435/308.1; 435/383; 435/29; 435/235.1; 435/255.7; 436/172; 436/57; 436/63

(58) Field of Classification Search ........................ None  
See application file for complete search history.

(56) References Cited

U.S. PATENT DOCUMENTS  
5,140,158 A * 8/1992 Post .............................. 250/281  
(Continued)

FOREIGN PATENT DOCUMENTS  
CA    2286601 A1    11/1998  
CA    2333201 A1    12/1999  
EP    1124939 A1     8/2001  
WO    2004020342 A2  3/2004

OTHER PUBLICATIONS

Li, Paul C.H., "The Microfluidic Biochip Advantage for Single-Cell Drug Discovery", Laboratory Focus, May 2005, 9(3): 8-9, 16, Promotive Communications Inc., Canada. Wheeler et al. (2003) "Microfluidic Device for Single-Cell Analysis" Anal. Chem. 75, 3581-3586.

*Primary Examiner* — Brian J Sines  
*Assistant Examiner* — Jennifer Wecker  
(74) *Attorney, Agent, or Firm* — Oyen Wiggs Green & Mutala LLP

(57) ABSTRACT

The invention relates to a microfluidic device comprising one or more fluid channels, one or more fluid ports, and a V-shaped particle retention structure. The fluid channel is generally opposite the particle retention structure, fluid ports are located between the fluid channel and the particle retention structure, and the particle retention structure has sloped side walls. Fluid, including reagents, can be delivered to the microfluidic device through the one or more fluid channels or the fluid ports. The invention also relates to methods of using the microfluidic device to monitor, observe, measure, or record a biological parameter of a particle, to separate a single particle from a group of particles, to culture a cell, to treat a particle, and to move a particle back and forth in the device.

39 Claims, 24 Drawing Sheets

U.S. PATENT DOCUMENTS

| | | |
|---|---|---|
| 5,914,262 A | 6/1999 | MacMichael et al. |
| 6,592,821 B1 | 7/2003 | Wada et al. |
| 6,692,952 B1 | 2/2004 | Braff et al. |
| 6,846,668 B1 * | 1/2005 | Garman et al. ............ 435/285.1 |
| 7,214,298 B2 * | 5/2007 | Spence et al. ................. 204/450 |
| 2004/0096960 A1 * | 5/2004 | Burd Mehta et al. ...... 435/287.2 |
| 2004/0235181 A1 * | 11/2004 | Arnold et al. ................... 436/63 |
| 2005/0207940 A1 * | 9/2005 | Butler et al. .................... 422/73 |

* cited by examiner

MICROFLUIDIC DEVICE AND METHOD OF USING SAME

RELATED APPLICATIONS

This application claims priority from U.S. Provisional Patent Application No. 60/588,317, filed 16 Jul. 2004.

TECHNICAL FIELD

This invention relates to microfluidic devices and methods of using the devices.

BACKGROUND

In recent years, microfluidic "chip" technology has been widely applied for biochemical analysis[1-3]. In particular, various microfluidic chip techniques for cellular biochemical analysis have been recently developed[4-19]. For on-chip experiments, transport and selection of cells has been mainly achieved by liquid flow[4-7, 9, 11, 20-22]. The main technical issues for successful cell biochemical studies include methods of retaining the cell and maintaining cell integrity during reagent delivery. To date, the major methods for cell immobilization include (1) cell adhesion[8, 23, 24], (2) physical retention within slit-type filters[25-28], weir-type filters[9, 11, 29, 30], or polymeric materials[31, 32], and (3) dielectrophoresis[33-35]. Adhesion or blocking of the cell usually generates a local force on a small part of the cell's surface rather than uniformly on the whole cell surface. Even if these particle retention strategies do not have any negative effect on a stationary cell, the liquid flow which is essential for transport of buffer and reagents to the cell might damage the cell. This is because the liquid flow always exerts a force on the cell. Therefore, a strong flow might damage the cell. On the other hand, the flow should not be too weak to ensure a sufficient flow for reagent delivery. To balance the force of the liquid flow, an opposite force needs to be applied to the cell.

Recently, biochemical studies have benefited from microfluidic chip techniques[1-3]. In particular, studies have been conducted on biological cells retained within microfluidic chips[4-19]. Most studies have been performed on groups of cells, and only a few studies have been performed on single cells[1, 6, 14, 19]. Moreover, microfluidic chip single-cell experiments generally have been limited to only one type of stimulus, or the experiments are only conducted once or over short periods of time. This provides insufficient information regarding single-cell biochemistry. In many cases useful information regarding single cells is unattainable by measurements performed on an ensemble of cells. Although there is a need to study groups of cells (e.g. to understand cell-cell interactions), it is also useful to conduct genuine single-cell microfluidic experiments.

SUMMARY

The invention relates to a microfluidic device comprising at least one first channel for introducing a first fluid into the device and a generally V-shaped particle retention structure for retaining a particle in the device, the particle retention structure having opposed wall portions and a central wall portion disposed between said opposed wall portions, wherein the particle retention structure is located generally opposite the first channel, and wherein the opposed and central wall portions have sloped side walls. One or more fluid ports are disposed between the first channel and the particle retention structure for delivering a second fluid to the microfluidic device or for allowing fluids to flow out of the device.

The sloped side walls can be curved, and they can be arcuately curved. When the side walls are arcuately curved, they can have an arc with a radius of curvature which is two or more times the width of the cell or particle to be retained in the microfluidic device. The first channel has a width greater than the width of the cell or particle to be retained in the microfluidic device. The central wall portion can have a width 2 or more times the width of the cell or particle. The V-shaped particle retention structure can have a height 2 or more times the width of the cell or particle. The width of the one or more fluid ports can be 2 or more times the width of the cell or particle and can be 4 times the width of the cell or particle. Lateral end portions of the particle retention structure can be angled between 0° and 180° relative to the opposed wall portions, and the angle can be 135°.

When fluid is delivered through the first channel, the fluid can form a zero speed point on the V-shaped particle retention structure. The zero speed point can be laterally shifted by an increase in delivery of a second fluid from one of the one or more fluid ports, due to an increase in electric potential or fluid potential in one of the one or more fluid ports.

The microfluidic device of the invention can also comprise a detection window proximate to the V-shaped particle retention structure for detecting biological parameters of the particle. The central wall portion can also comprise one or more grooves.

The invention also relates to a microfluidic device comprising two or more particle retention structures, two or more fluid ports, and two or more first fluid channels.

The invention also relates to a method of monitoring, observing, measuring, or recording a biological parameter of a particle using the microfluidic device of the invention. The biological parameter can be any parameter, including size, morphology, growth rate, biomarkers, influx of a substance, efflux of a substance, reaction of the particle to one or more stimuli, or reaction of the particle to changes in the environment of the particle. The substance can be a coloured substance, a chromogenic substance, a fluorescent substance, a fluorescent-labelled substance, and a radio-labeled substance, or any other substance. Kinetic or thermodynamic parameters can be mathematically extracted from the biological parameters of the cell or particle. The biological parameter can be monitored, observed, measured, or recorded in real-time and over extended periods of time.

The invention also relates to a method of culturing a cell comprising growing the cell in a microfluidic device of the invention, a method of treating a particle with a fluid in the microfluidic device, and a method of separating a particle from a group of particles using the microfluidic device.

The invention also relates to a method of moving a particle in a microfluidic device comprising isolating the particle in a zero speed point and moving the zero speed point in the microfluidic device.

The invention also relates to methods of monitoring the synthesis and growth of proteins, protein crystals, nanoparticles or other particles.

The microfluidic device and methods can also be used with any type of particle, such as cells, beads, viral particles, proteins, protein crystals, nanoparticles or other particles. The cells can be prokaryotic cells or eukaryotic cells, such as yeast cells, fungal cells, plant cells, animal cells or other cells.

BRIEF DESCRIPTION OF DRAWINGS

(FIG. 1A)

The microfluidic device contains ports 12 and 14 for cell introduction (from either port 12 or 14) and a channel 16 (40 μm wide) for delivery of buffer or reagent solutions. The V-shaped particle retention structure, which is opposite to the reagent channel 16, consists of opposed wall portions with a central wall portion in between. Fluorescent signal was detected within the detection window (white rectangle shown in the inset) by a photomultiplier tube (PMT). A single yeast cell lies freely on the sloped wall of 15 μm radius (see inset) balanced by the liquid flow. (B) Cell introduction: The liquid flow from the left carries a group of cells to the particle retention structure. (C) Cell selection: The liquid flow from channel 16 separates the cells and sends the desired cell downward to the detection window. Liquid flow can be driven by either fluid potential (<1 mm) or electric potential difference (0.01~1.5 kV). "+" shows the high potential. (D) illustrates one embodiment of the microfluidice device. (E) is a cross-sectional view of one embodiment of the microfluidic device taken at line S1 as indicated in FIG. 1D. (F) is a cross-sectional view taken at line S2. (G) is a magnified view of a portion of FIG. 1E. (H) is a perspective view of an embodiment of a microfluidic device.

Figure 1:
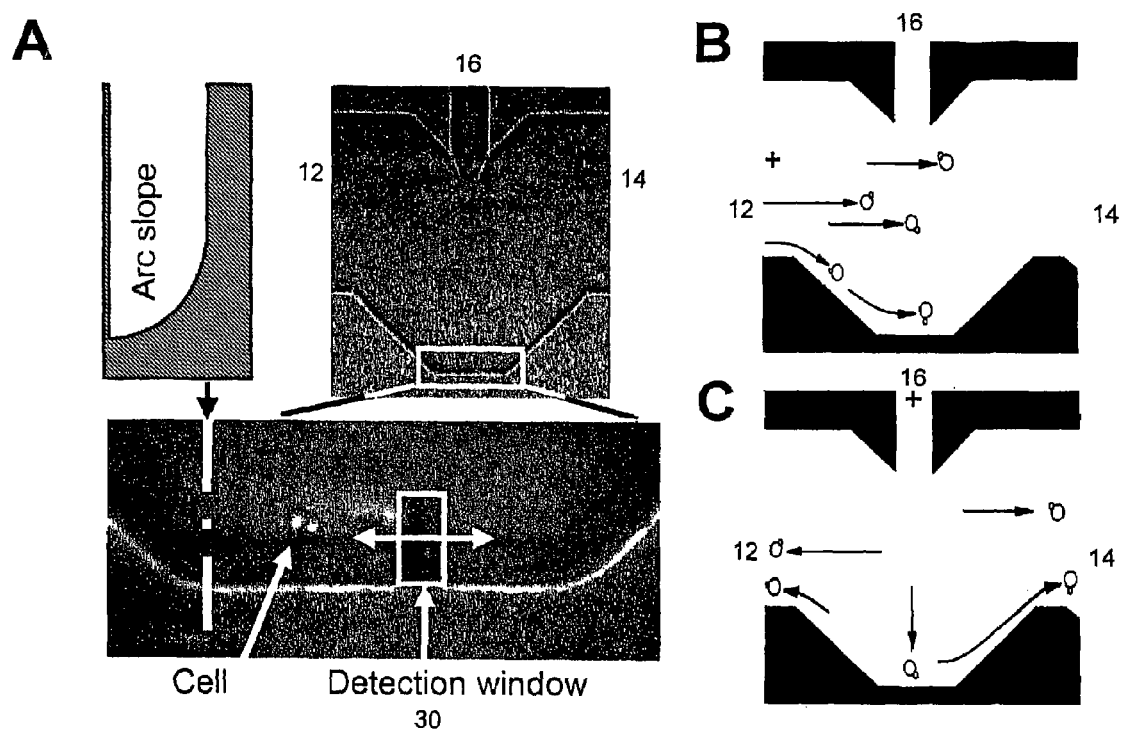
FIG. 1 illustrates the design of an embodiment of the microfluidic device and cell selection mechanism.
Figure 1:
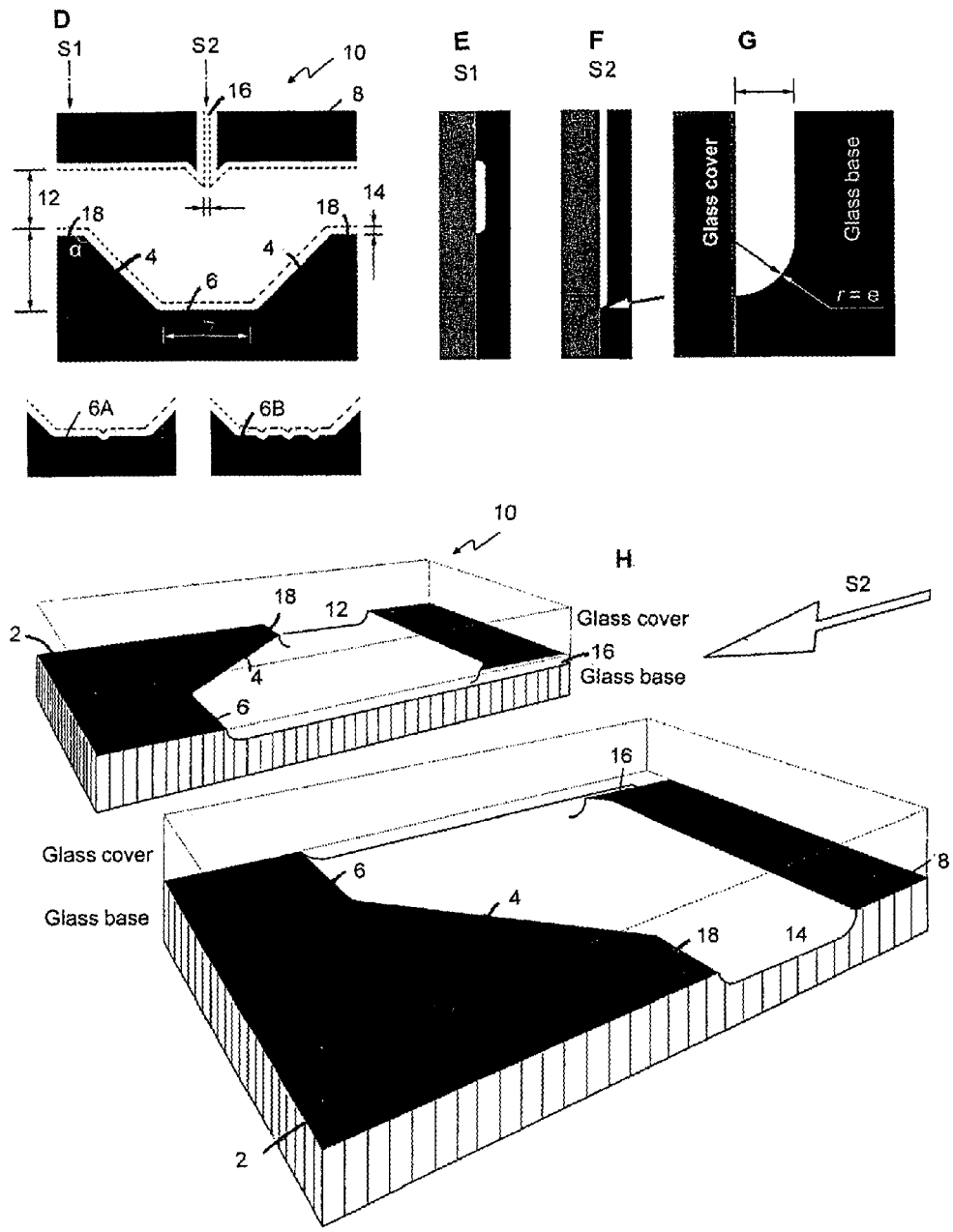
Figure 2:
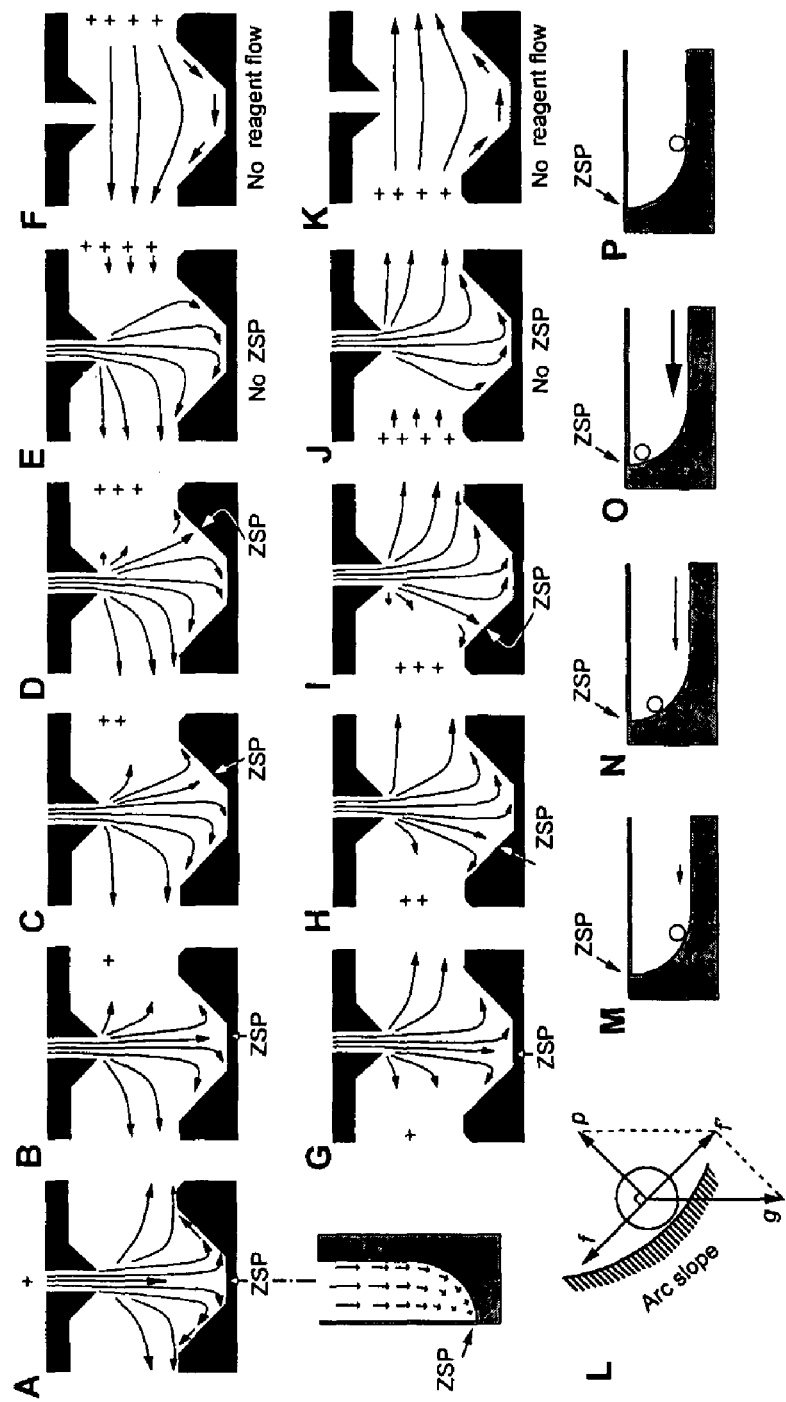

FIG. 2 illustrates the 3-dimensional flow control achieved by an embodiment of the microfluidic device. (A) A two-dimensional channel flow field was created by the flow from channel 16. There is a zero speed point (ZSP) where the flow speed decreases nearly to zero. When there is no flow from ports 12 and 14, the ZSP is in the middle, directly opposite to channel 16 (the notations of 12, 14, 16 have been described in FIG. 1). The third dimensional flow field is along the sloped side walls of the particle retention structure as shown in the cross section diagram in the inset. (B-E) As the fluid potential from the right is increased, the shape of the flow field changes and the ZSP moves to the right. (F) As shown when there is no reagent flow from channel 16, the flow field can be driven by the fluid potential from the right. (G-J) The flow field shape also changes when fluid potential from the left is increased. (K) As shown when there is no reagent flow from channel 16, the flow field can be driven by the fluid potential from the left. (L) The third dimensional flow field along the sloped side walls of the particle retention structure results in the cell balancing on the sloped side walls. The forces between the upward force exerted by the liquid flow (f), downward gravitational force (g) on the cell, and the reaction force from the sloping wall (P) are balanced on the cell. (M-O) The position of the cell on the sloped side walls changes as the reagent flow from channel 16 increases. (P) The position of the cell when there was no flow.

Figure 3:
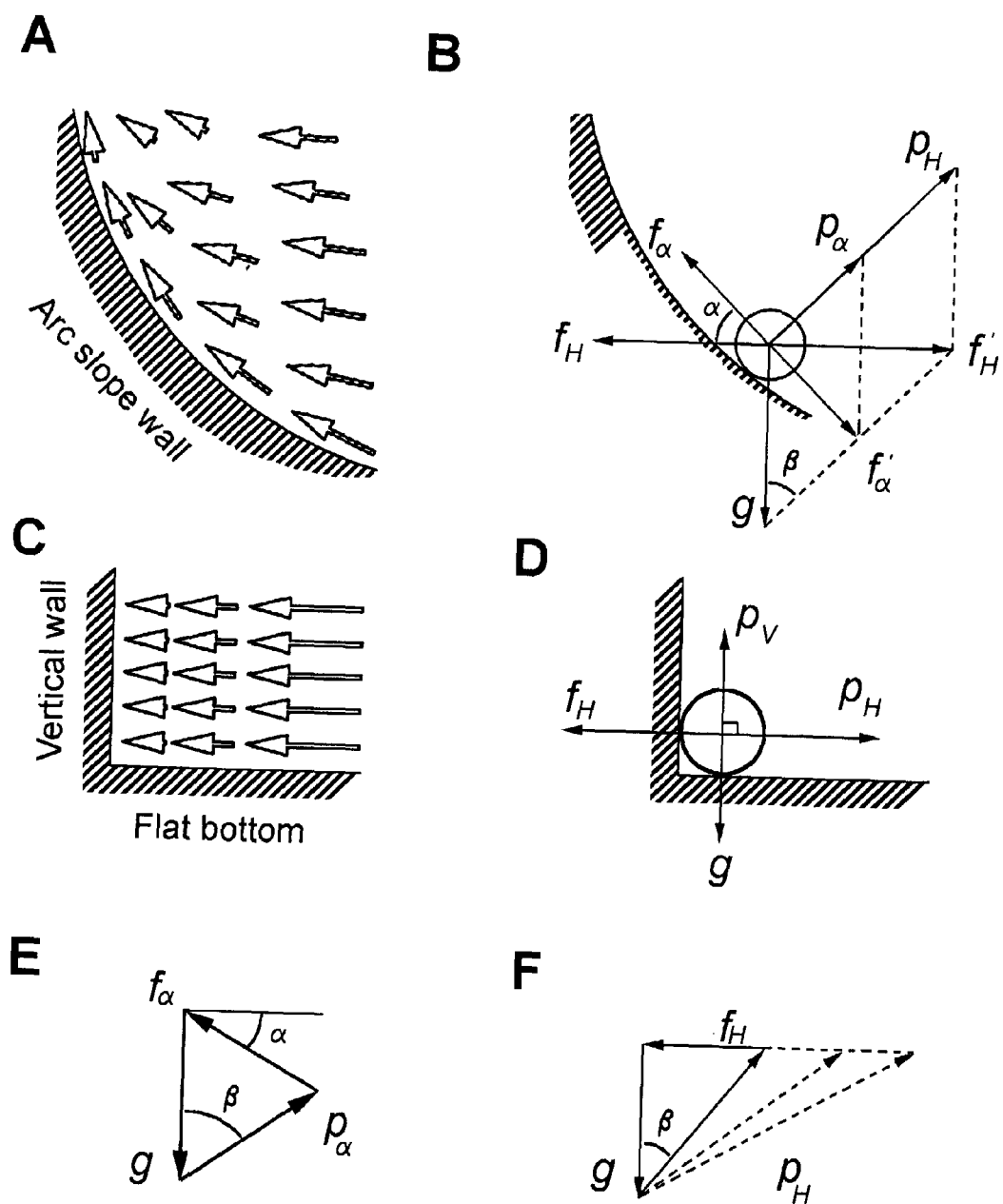

FIG. 3 illustrates the forces exerted on a cell contained within the microfluidic device of the invention. (A) The different directions and strengths of fluid flowing near the sloped side walls of the particle retention structure are shown. (B) The forces exerted on a cell balanced on the sloped side walls of the particle retention structure; g: The cell's gravity (buoyancy subtracted); $f_\alpha$: The force exerted by the flow at an angle ($\alpha$); $f_H$: The force exerted by horizontal fluid flow (i.e. $\alpha=0$); $P_\alpha$: The reaction force of the sloped side walls to the cell for a flow directed at an angle ($\alpha$); $P_H$: The reaction force of the sloped side walls to the cell for a horizontal flow. (C) The direction and strength of liquid flowing near a vertical wall. (D) The forces exerted on a cell balanced against perpendicular walls. $P_v$: The reaction force of the bottom wall to gravity; $P_H$: The reaction force of the vertical wall to the cell due to horizontal flow. (E) The force relationship between g, $f_\alpha$ and $P_\alpha$ as given in (B). (F) The force relationship between g, $f_H$ and $P_H$ when a cell is balanced on arcuately slopped side walls with an increased angle of the slope ($\beta$).

Figure 4:
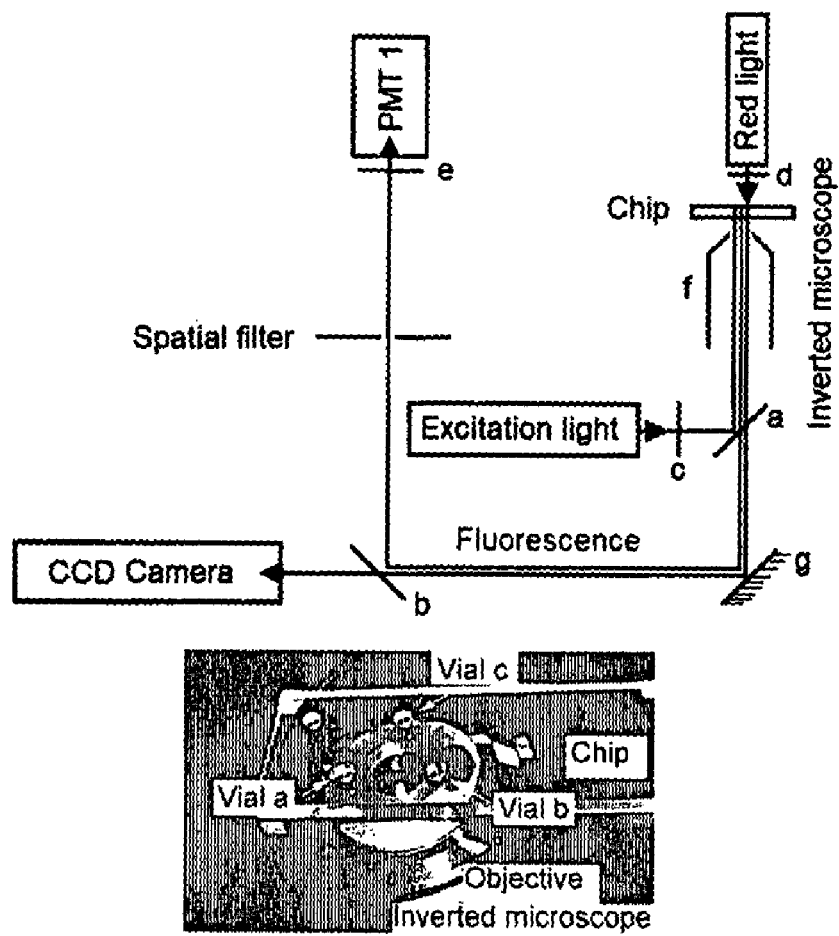

FIG. 4 is a schematic diagram of an optical measurement arrangement. The setup includes an inverted microscope and the associated optics. 20: dichroic filter 1 (495 nm); 22: dichroic filter 2 (540 nm); 24: band-pass filter (470 nm/40 nm); 26: long pass filter (645 nm); 28: band pass filter (525 nm/50 nm); 30: microscope objective (ELWD, 40×/0.60); 32: mirror. The first optical path (red light, to 26, to microfluidic device, to 30, to 20, to 32, to 22, and to CCD camera) was used for bright-field optical observation. The second optical path (excitation light, to 24, to 20, to 30, to microfluidic device, to 30, to 32, to 22, to 28, and to PMT) was used for fluorescent measurement. The embodiment of the microfluidic device as shown was been used in single-cell experiments. The width of the microfluidic device is 16 mm. In the photograph of the microfluidic device, vial a is connected to port 12, vial b is connected to port 14, and vial c is connected to channel 16.

Figure 5:
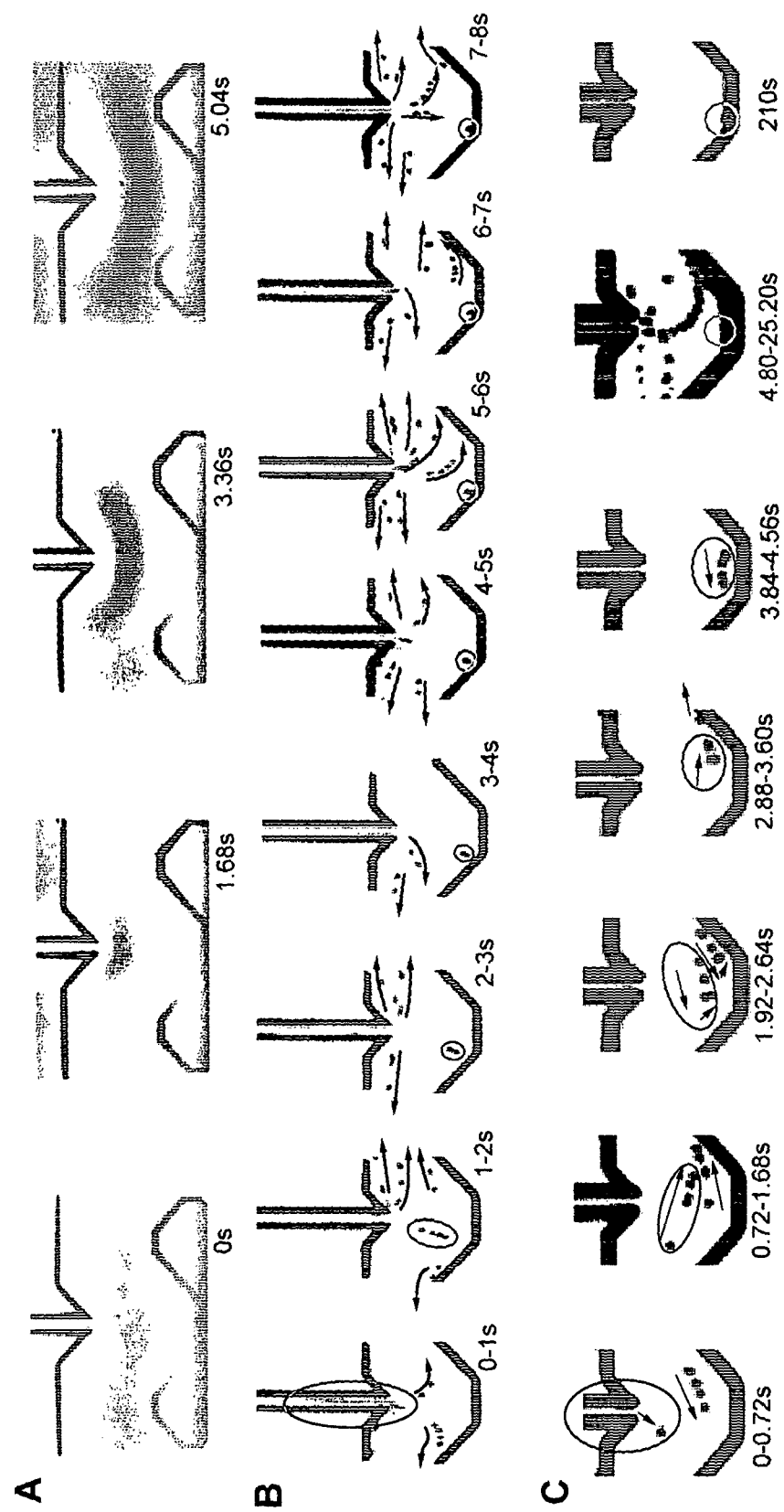

FIG. 5 contains a series of images demonstrating the 3-dimensional fluid flow in the microfluidic device. (A) Buffer with FDA (12 μM) was injected from channel 16 toward the particle retention structure. The solution front expanded downward as observed by the inverted microscope in the phase-contrast mode. (B) The beads traveled from channel 16 towards the particle retention structure. Images were captured every 0.24 s and overlaid. Therefore, in each of the frames, four beads represent the travel path of one bead in each of the images over 0.72 s. The distance between any two closest beads illustrates that bead's length of travel within 0.24 s. Beads traveled quickly in channel 16 but their rate of travel slowed when they approached the particle retention structure. The beads demonstrated the flow fields as depicted in FIG. 2H. (C) Selection, retention and immobilization of a bead using fluid flow. The desired bead to be selected is circled. Again, bead images were captured every 0.24 s, and images are overlaid to show their positions every 0.24 s.

Figure 6:
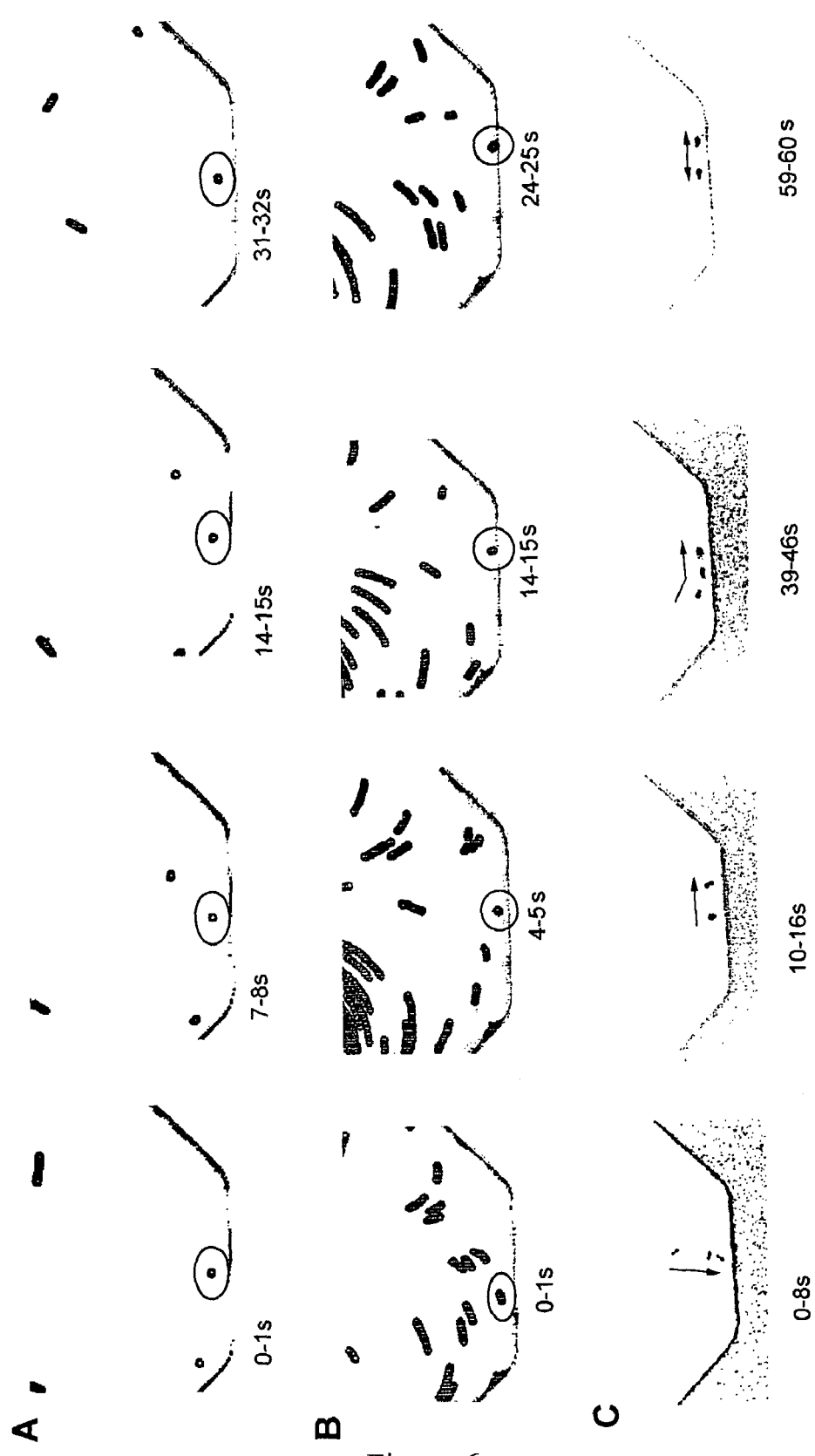

FIG. 6 contains images of beads and yeast cells balanced on the sloped side walls of the particle retention structure. (A) A bead balanced on the sloped side walls in the presence of a weak reagent flow. Trails of the beads represent movement of the beads in 0.08 s intervals. (B) When flow was increased, the bead moved higher up on the sloped side walls to a new balanced forced position. (C) A budding yeast cell moving towards the sloped side wall until balanced against the side wall (0-8 s). The three dots represent images of the same single cell at different times, which demonstrate how the fluorescent cell is scanned. The cell was scanned to the right during fluorescent detection (10-16 s). In a stronger reagent flow, the cell moved further up the sloped side wall to a new balanced force position (39-46 s). The cell was scanned at its new force balance position during fluorescent detection (59-60 s).

Figure 7:
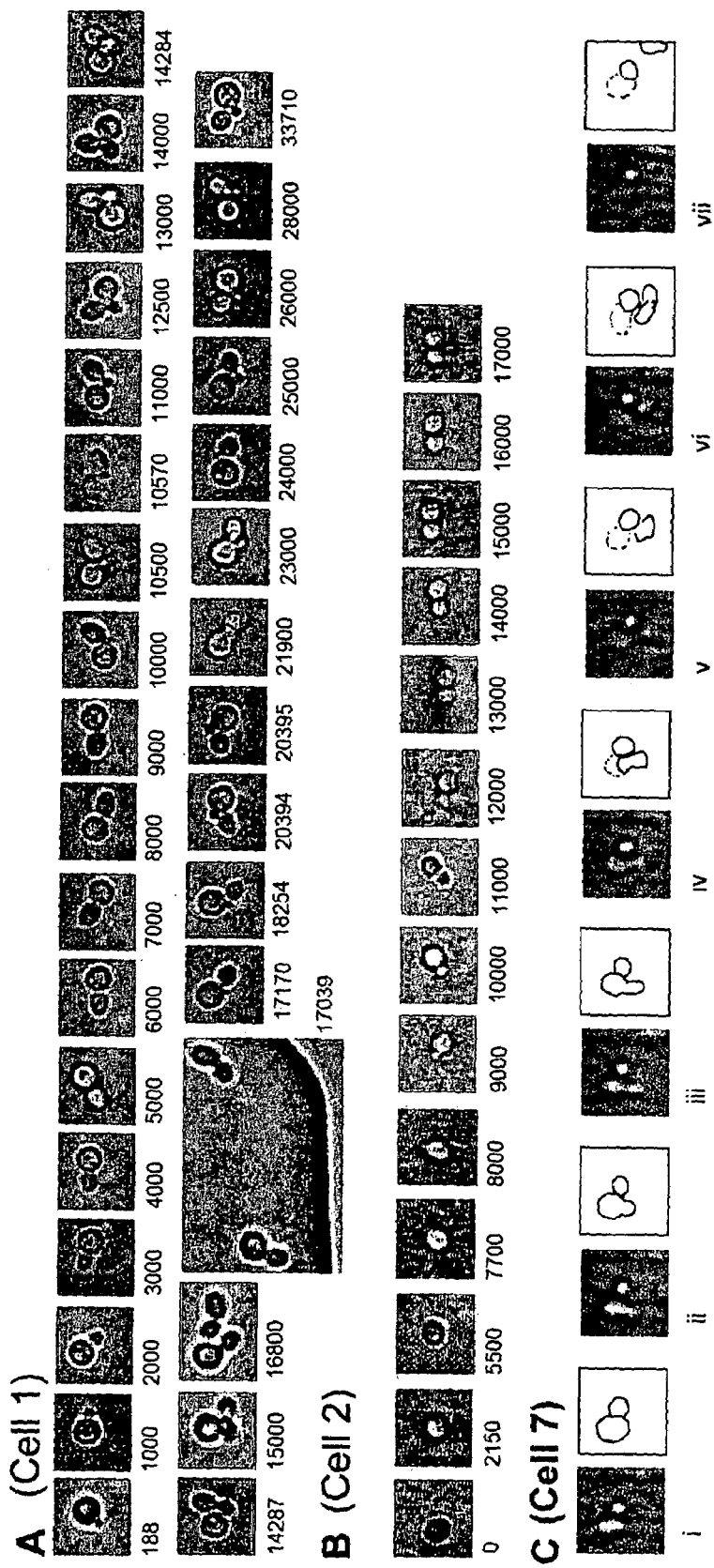

FIG. 7 depicts a series of on-chip cell culture images captured from video recordings (time in seconds). (A) A yeast cell (cell 1) grown in the microfluidic device (at 24° C.). The cell divided twice before experiments on FDA metabolism were performed on it. (B) Another yeast cell (cell 2) picked directly from a cell colony was cultured in the microfluidic device at 24° C. It was grown for 17000 s. (C) Another yeast cell (cell 7) had its cell wall removed on-chip cell. The process had a duration of 3.84 s. Each photo is accompanied by a schematic diagram to illustrate the various steps during the cell wall removal process.

Figure 8:
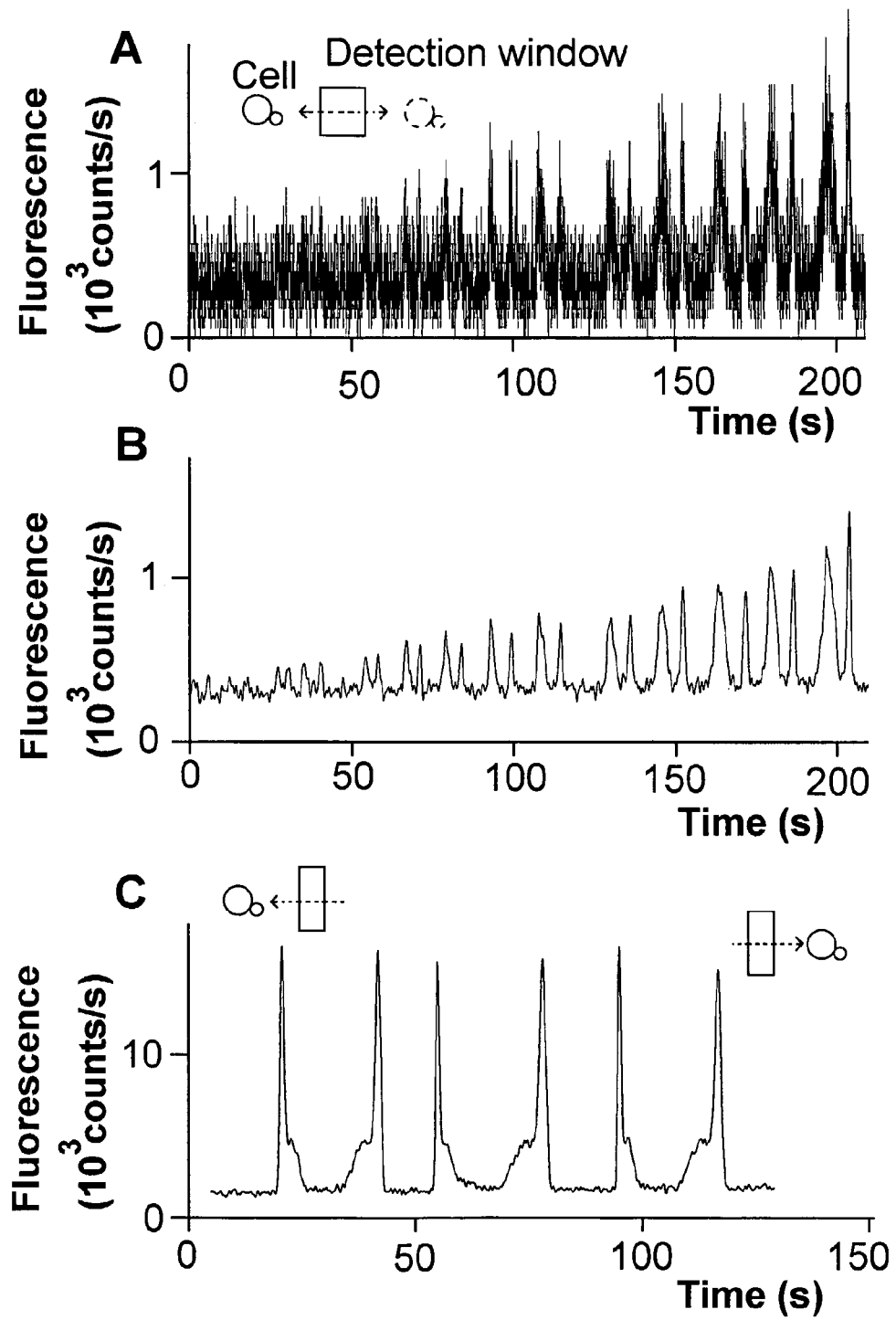

FIG. 8 depicts the fluoresence signal generated by a yeast cell detected through cell scanning, and noise filtering. (A) A fluorescent yeast cell travelling back and forth through the detection window generated peaks over the background. (B) The peak signal became clearer after filtering the noise (>2.5 Hz). (C) The use of a narrower detection window allowed a mother yeast cell to be distinguished from its daughter yeast cell, as fluorescent signal was depicted by a peak (generated by the larger mother cell) and a shoulder (generated by the smaller daughter cell).

Figure 9:
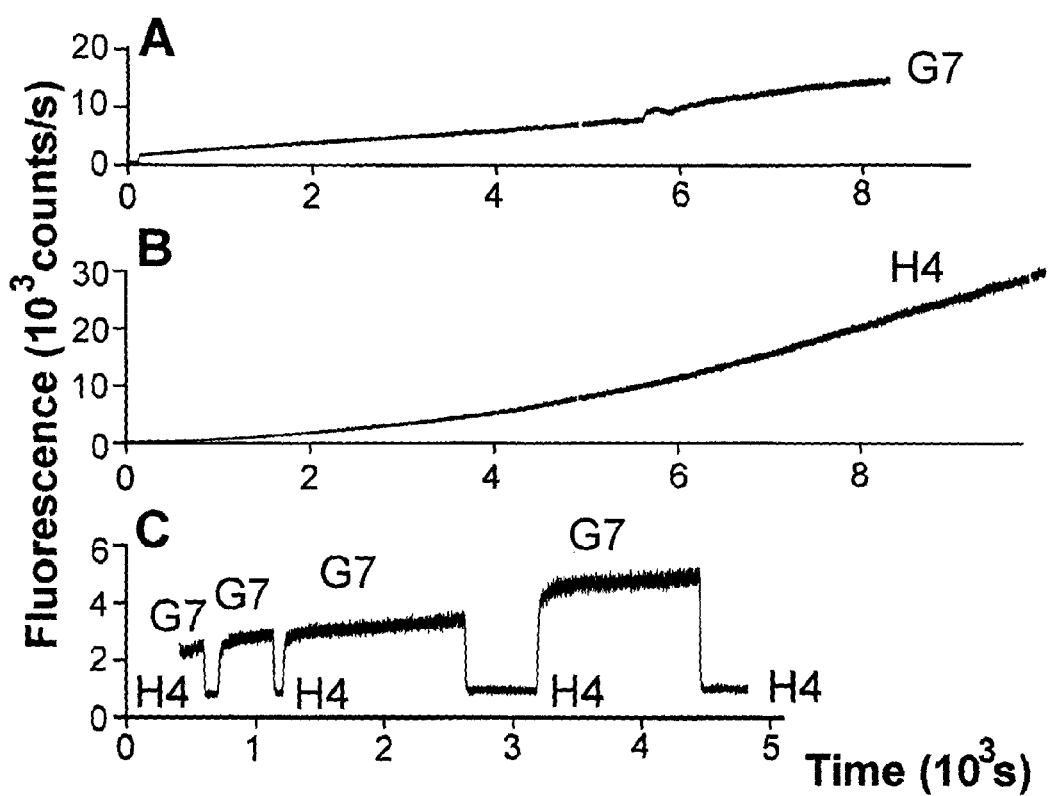

FIG. 9 depicts the background fluorescence of buffer solutions (without cells) stored in a microfluid device of the invention. The gradual increase in fluorescence is due to the slow hydrolysis of FDA to produce fluorescein in the aqueous buffers. (A) Buffer G7; (B) Buffer H4; (C) Changing between G7 and H4.

Figure 10:
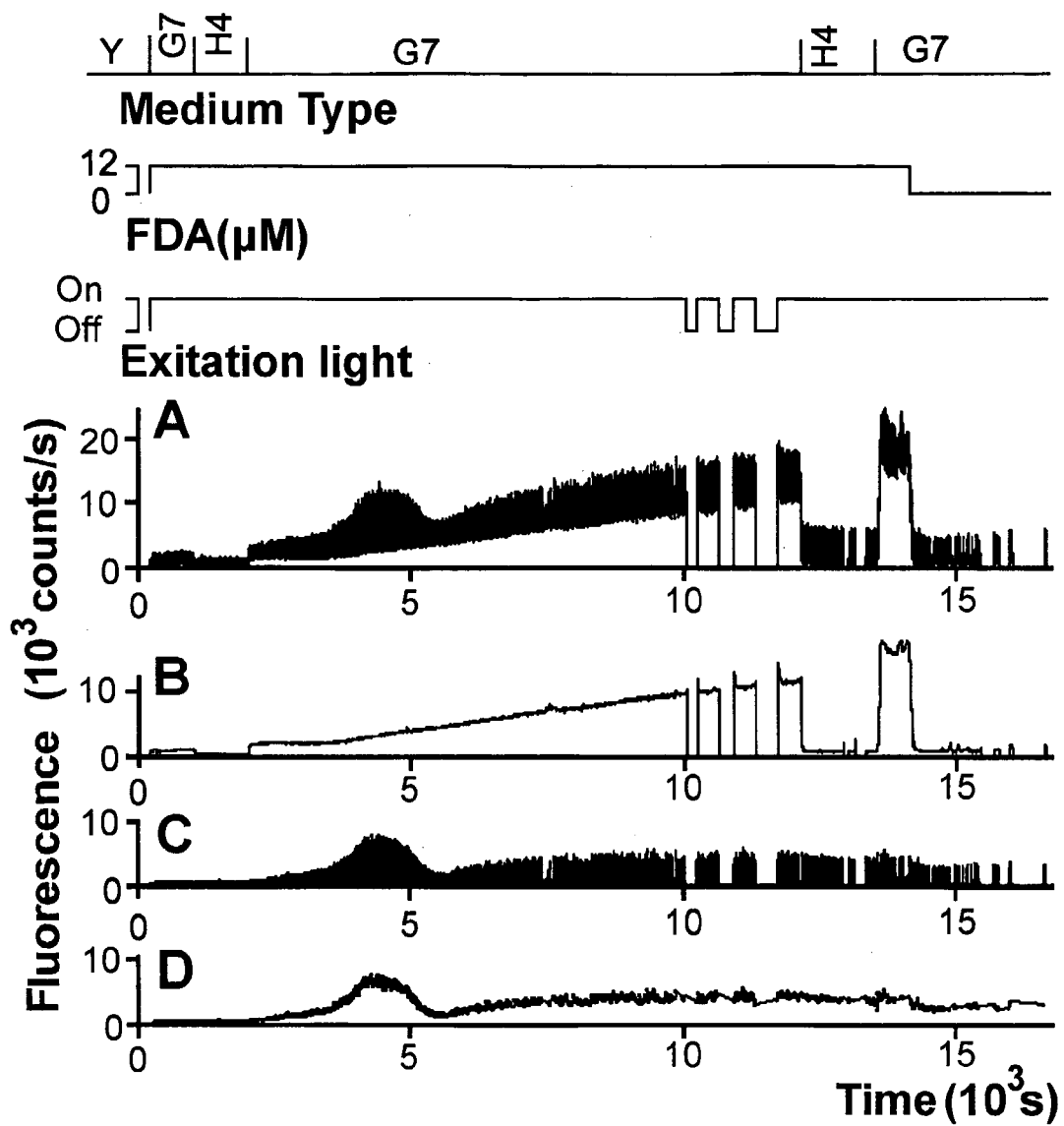

FIG. 10 depicts background fluorescence signals which are used to correct data signals. Background correction was applied to an experiment with a yeast cell (cell 5). (A) Peaks due to cell fluorescence plus background. (B) Background baseline extracted from (A). (C) Cell fluorescence peaks after background subtraction, (D) Peak envelope of all fluorescence peaks. The two reagent scales indicate the buffer types and the FDA concentrations. The excitation light scale indicates when the excitation light was turned off or on.

Figure 11:
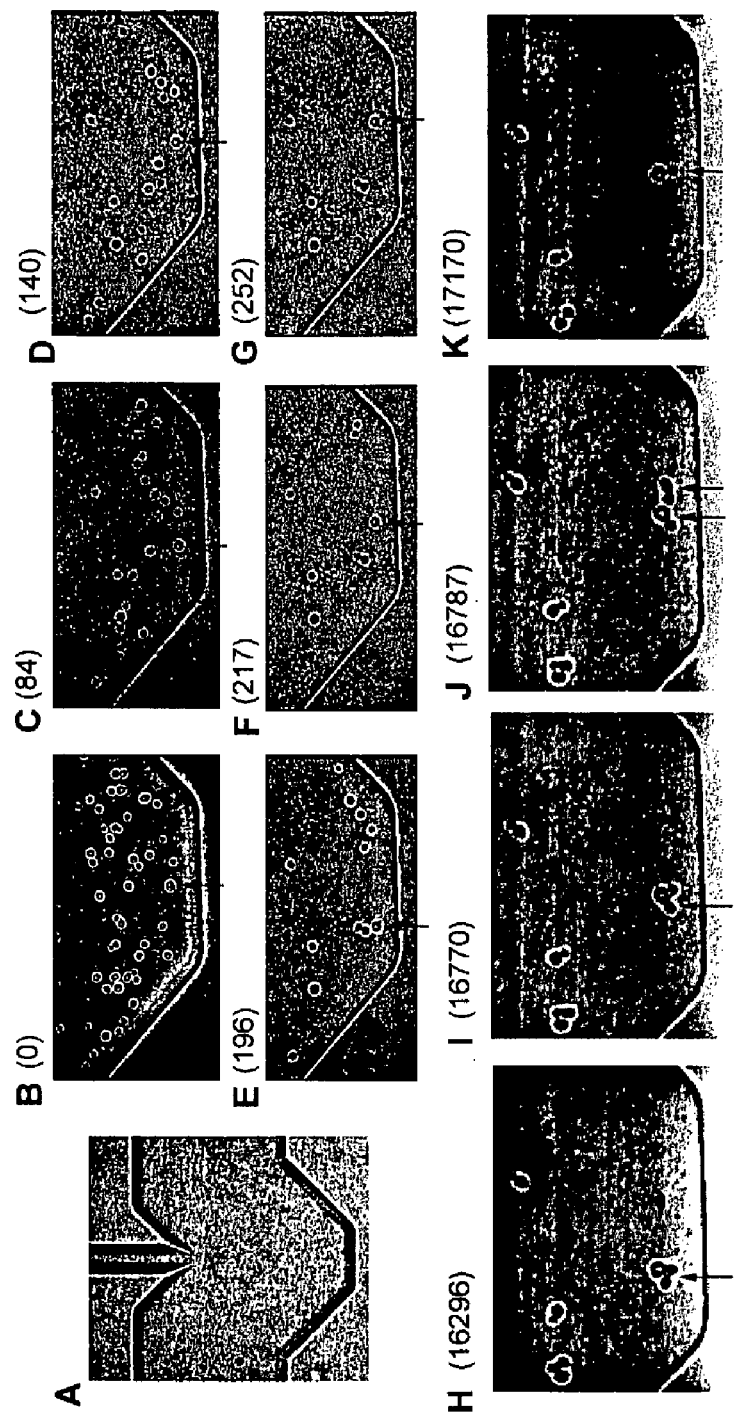

FIG. 11 consists of a series of images of a yeast cell in cell culture in a microfluidic device and subsequent to on-chip cell selection (cell 1 referred to in FIG. 12A, time in seconds). (A) The microfluidic device. (B-G) The cell was selected from a group of cells. (H-K) The daughter cells escaped from the mother yeast cell in the reagent flow. This cell (cell 1) has also been described in FIG. 7A.

Figure 12:
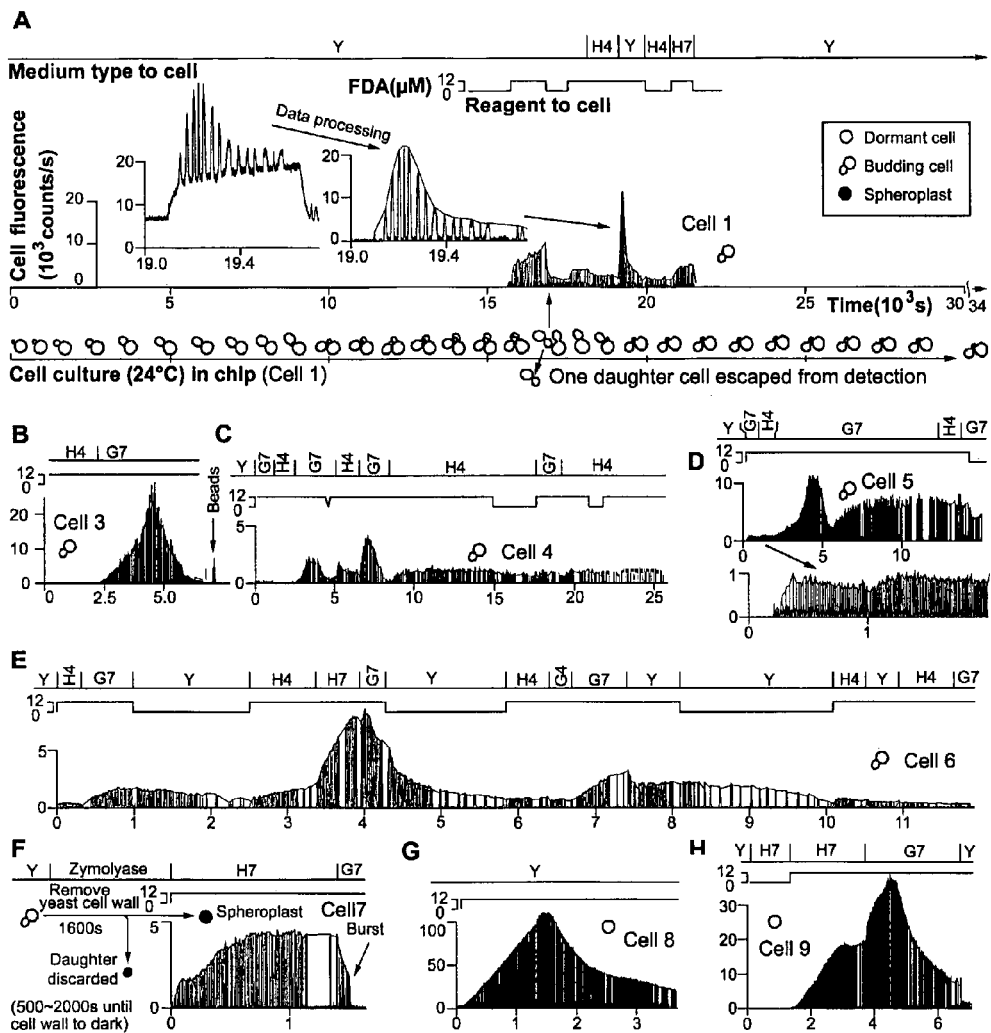

FIG. 12 depicts fluorescence signals produced by yeast cells during FDA metabolism. (A) On-chip cell culture (Cell 1), medium and reagent change, fluorescence detection and data processing. (B) (C) (D) (E) FDA experiments on other single budding yeast cells. (F) FDA experiment on a spheroplast after on-chip cell wall removal. (G) (H) FDA experiments on single dormant yeast cells. Three scales of buffer types, FDA concentrations (0 or 12 mM) and cell fluorescence intensity (103 counts per second) were the same as those in (A). Y: Yeast cell culture medium (YPD). H4 and H7: 285 mM HEPES, and at pH=4.3 and pH=7.3, respectively. G7 and G4: 28.5 mM HEPES plus 256 mM D-glucose, and at pH 7.3 and pH=4.3, respectively. Beads: fluorescent beads were used for calibration at 8 ks. All results are shown after background correction, as depicted in (A).

Figure 13:
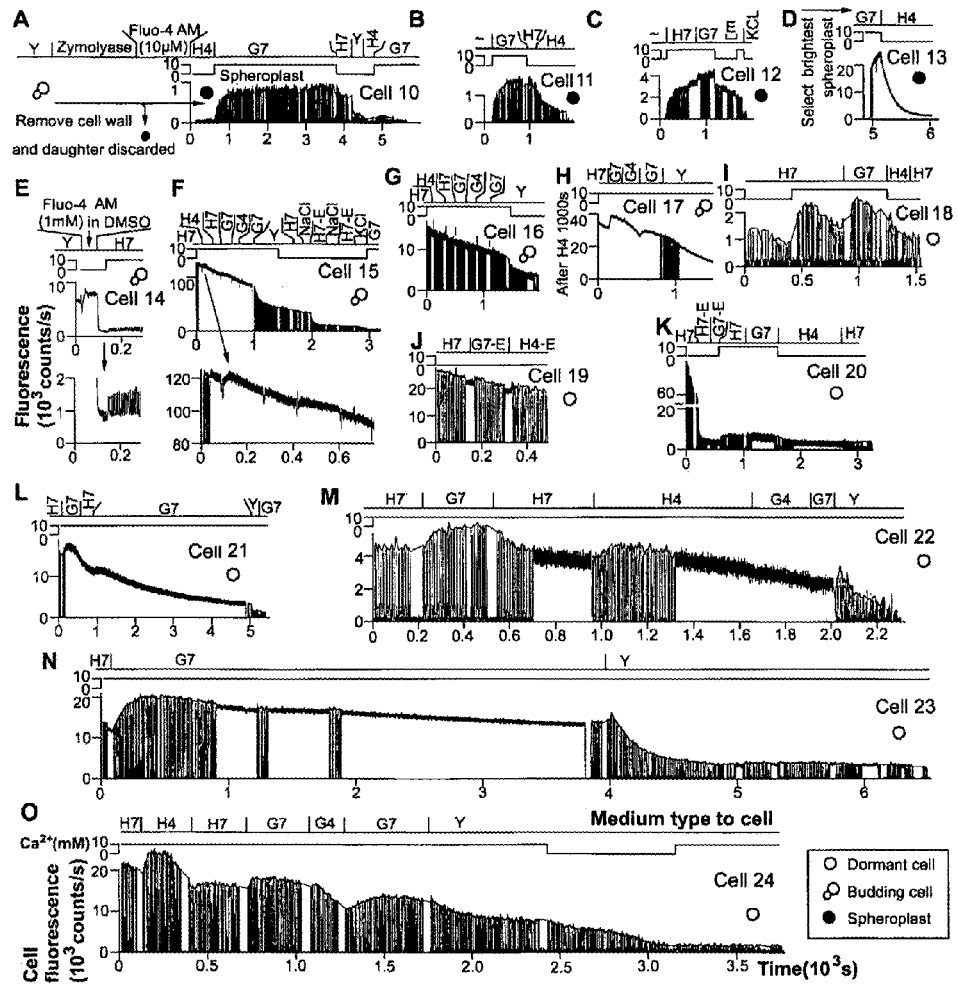

FIG. 13 depicts fluorescence signals detected in single yeast cells during $Ca^{2+}$ mobilization tracking tests. (A) (B) (C) Experiments after on-chip cell selection, followed by on-chip cell wall removal and Fluo-4-AM loading. (D) Experiments after off-chip cell wall removal and Fluo-4 AM loading, followed by on-chip cell selection. (E) Experiments after on-chip cell selection, followed by direct on-chip high-concentration Fluo-4 AM (in DMSO) loading. (F-O) Experiments after off-chip high-concentration (1 mM in DMSO) Fluo-4 AM loading followed by on-chip cell selection. All three scales of buffer types, $Ca^{2+}$ concentration and fluorescent intensity were the same as in FIG. 3O. Y: culture medium (YPD); E: EDTA. All results shown are after background correction (shown in FIG. 2A) except (E).

Figure 14:
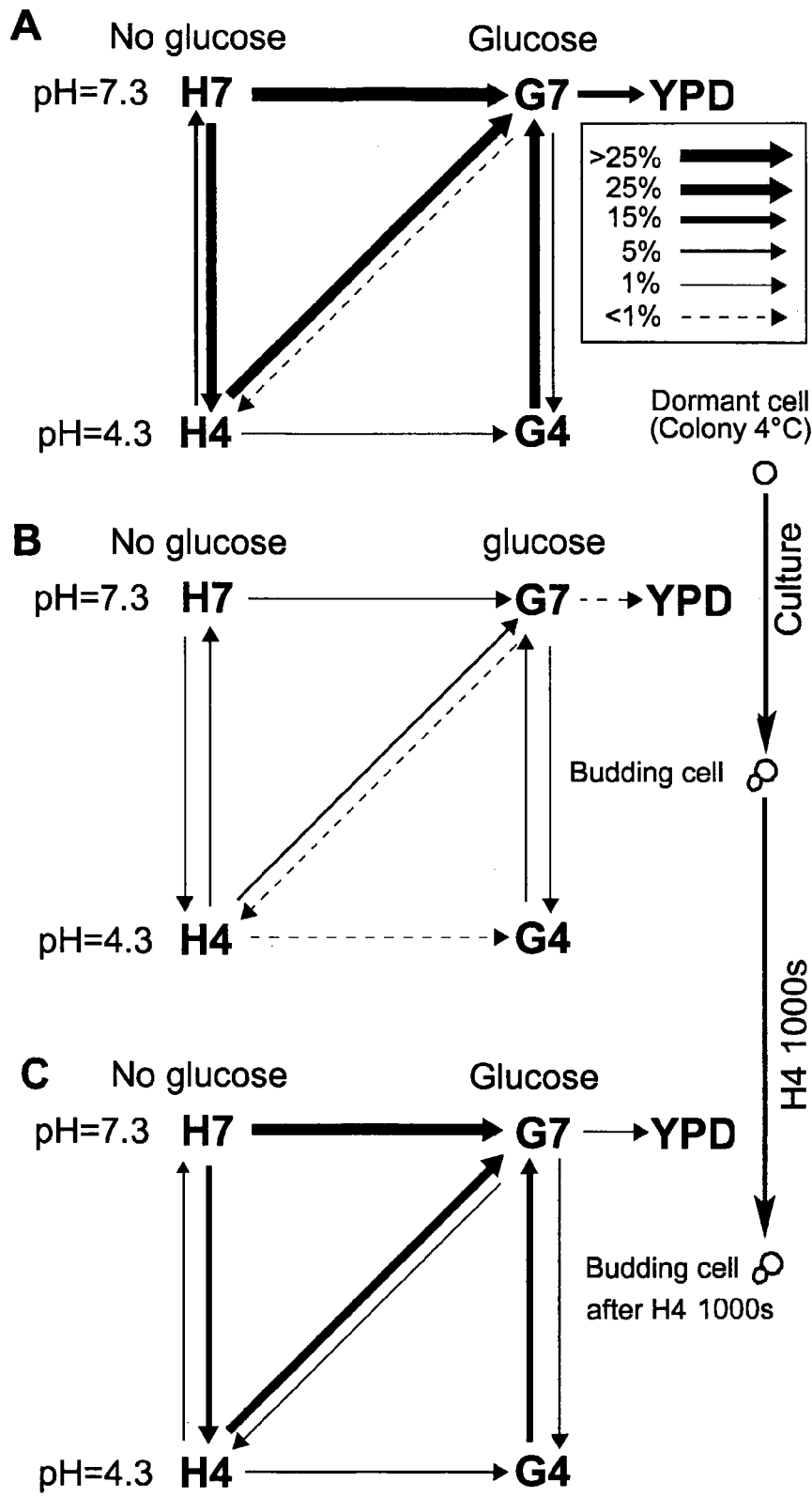

FIG. 14 depicts calcium mobilizations in three kinds of single yeast cells (dormant, budding and treated budding) in response to glucose and pH changes. Arrows show the changes of buffer types and the associated changes of intracellular fluorescence ($Ca^{2+}$-Fluo-4). The line widths of the arrows indicate the fluorescence changes, which are given as percentages, in the legend.

Figure 15:
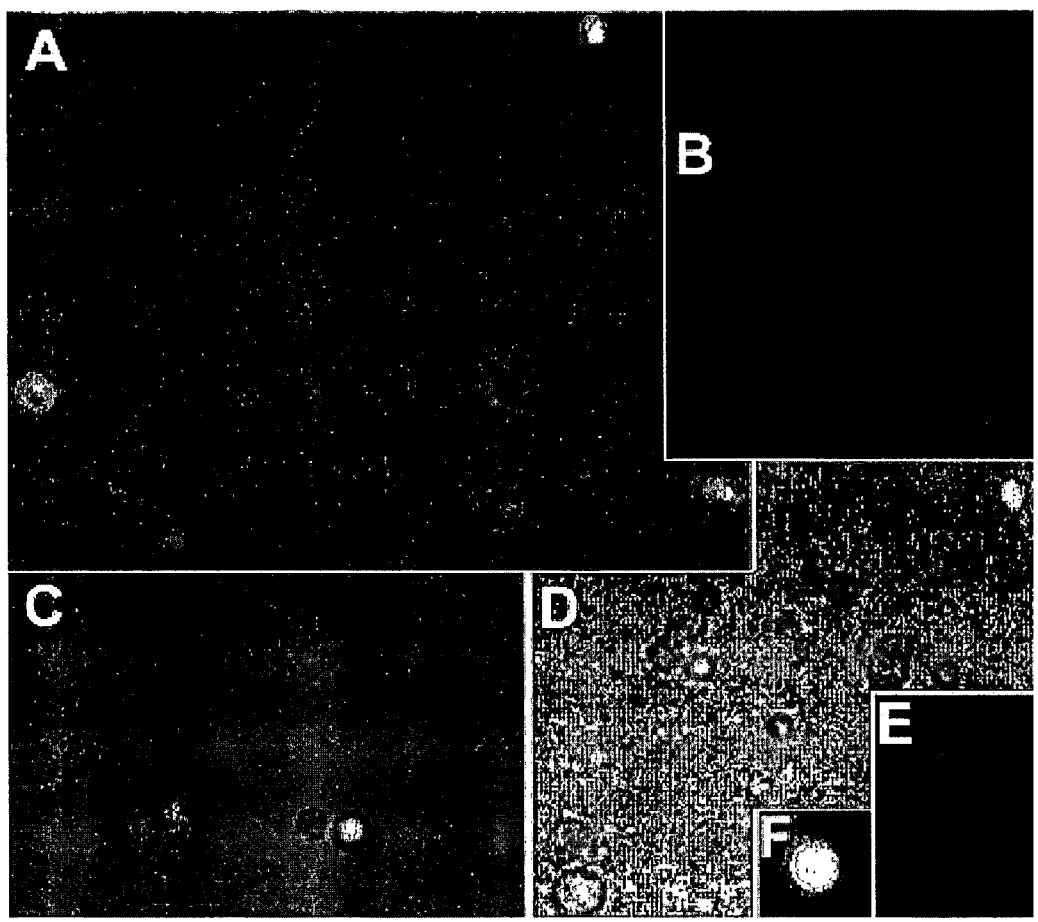

FIG. 15 is a comparison of yeast cell images which illustrate the differences in fluorescence of cells grown in different conditions. (A-B) Fluorescence due to fluorescein formed after G7 (12 μM FDA) incubation for 1.5 ks; (A) dormant cells, (B) budding cells after H4 incubation for 1 ks. (C-E) Fluorescence due to $Ca^{2+}$-Fluo-4 formed after 4 s off-chip loading of high-concentration Fluo-4-AM/DMSO (1 mM), followed by 0.5 ks treatment of $Ca^{2+}$ (10 mM in G7); (C) dormant cells, (D, E) budding cells. (F) Fluorescence due to a 6-μm fluorescent bead.

Figure 16:
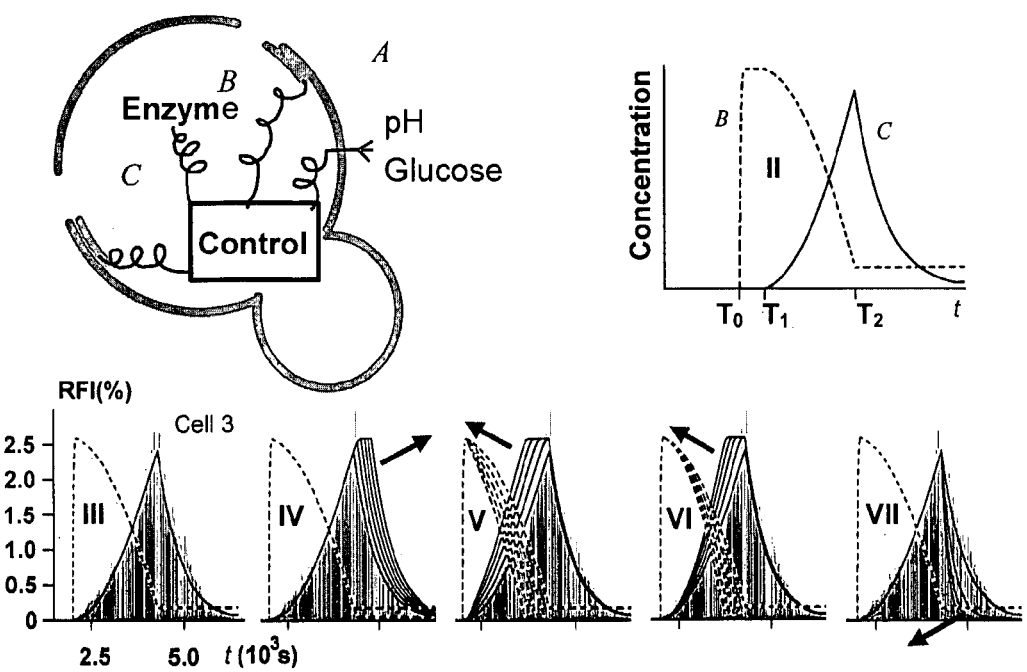

FIG. 16 illustrates a mathematical model for FDA metabolism in a single cell (Cell 3). Curve-fitting and sensitivity tests: (I) there are 3 cellular processes, namely influx, hydrolysis and efflux. The yeast cell exerts control over the influx of FDA (A), hydrolysis of FDA (B), to form fluorescein (C) and efflux of fluorescein in response to the stimuli of pH and glucose. (II) Intracellular concentrations of FDA (B) and fluorescein (C). Only C was experimentally measured. $T_0$, $T_1$ and $T_2$ represented the time (s) when buffer change, peak increase and peak decrease occurred, respectively. (III) Curve fitting: in the graph, dashed and solid lines represent the modelled amount of intracellular FDA and fluorescein respectively, and striped areas underneath the solid lines represent the signal peaks for the measured amount of fluorescein, which were calibrated with a fluorescent bead of known intensity. Note that this experiment has been previously represented in FIG. 2B. (IV, V, VI, VII) Sensitivity tests of the model: The effects on the model lines are depicted as a series of black lines. When one parameter is changed in each of the following cases, (IV) $T_2$-$T_1$: 2300-2700 s, (V) $V_{m0}$: 0.001-0.005 μM $s^{-1}$, (VI) k: $(4-8) \times 10^{-6}$ μM $s^{-2}$ (VII) $V_e$: 1-4 μM μm $s^{-1}$. (RFI: relative fluorescent intensity in which 1% represents the fluorescence resulted from full hydrolysis products from $6 \times 10^{-19}$ mol of FDA).

Figure 17:
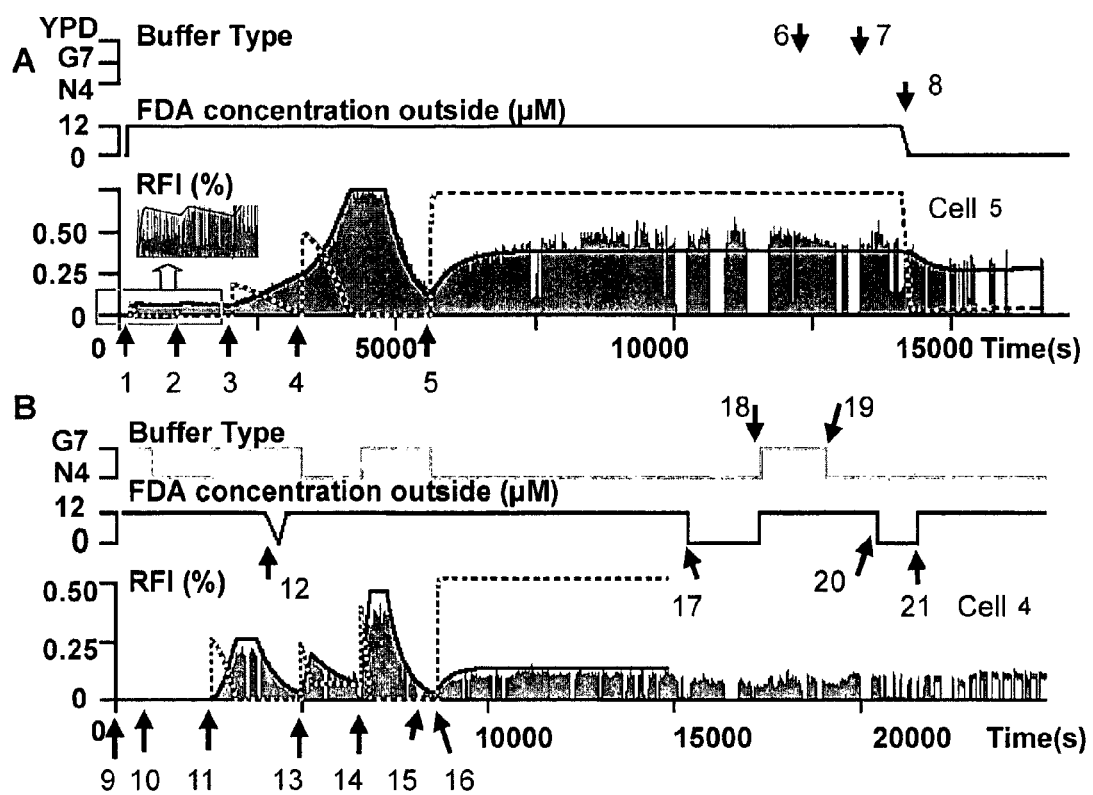

FIG. 17 illustrates fluorescence of cells under various stimuli. The curve fittings were performed on (A) cell 4 and (B) cell 5 which underwent a series of changes due to pH and glucose stimuli. Dashed and solid lines represent the modelled amount of intracellular FDA and fluorescein respectively, and striped areas underneath the solid lines represent the signal peaks for the measured amount of fluorescein. Changes of buffer type or FDA concentration are indicated by arrows with numbers, and are described in the text. Note that (A) has also been described in FIG. 12D, and (B) has been described in FIG. 12C.

Figure 18:
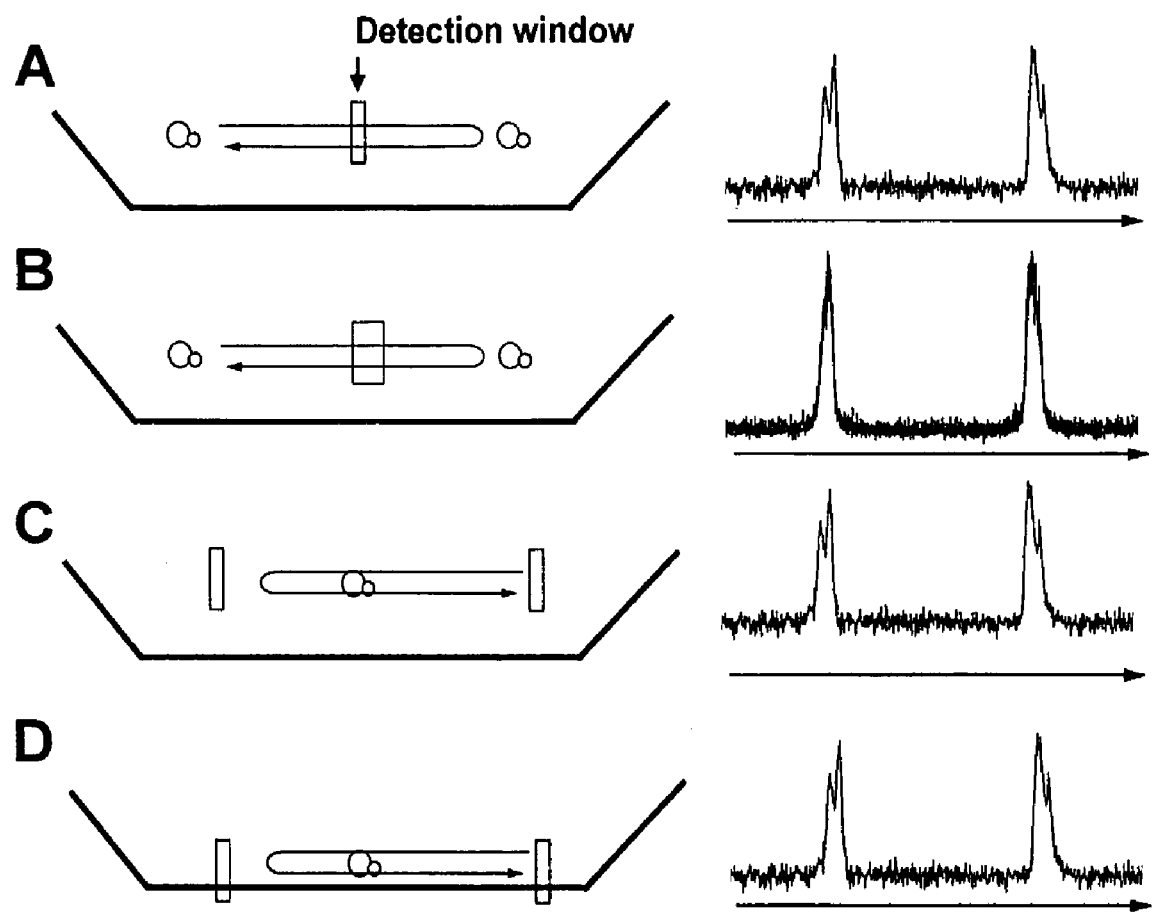

FIG. 18 illustrates different types of cell scanning. The left series of illustrations of A-D show the different scanning paths (the arrows indicates the moving cells in A and B or the moving detection windows in C and D) in the cell retention structure. The right series of illustrations of A-D show the measurement results.

Figure 19:
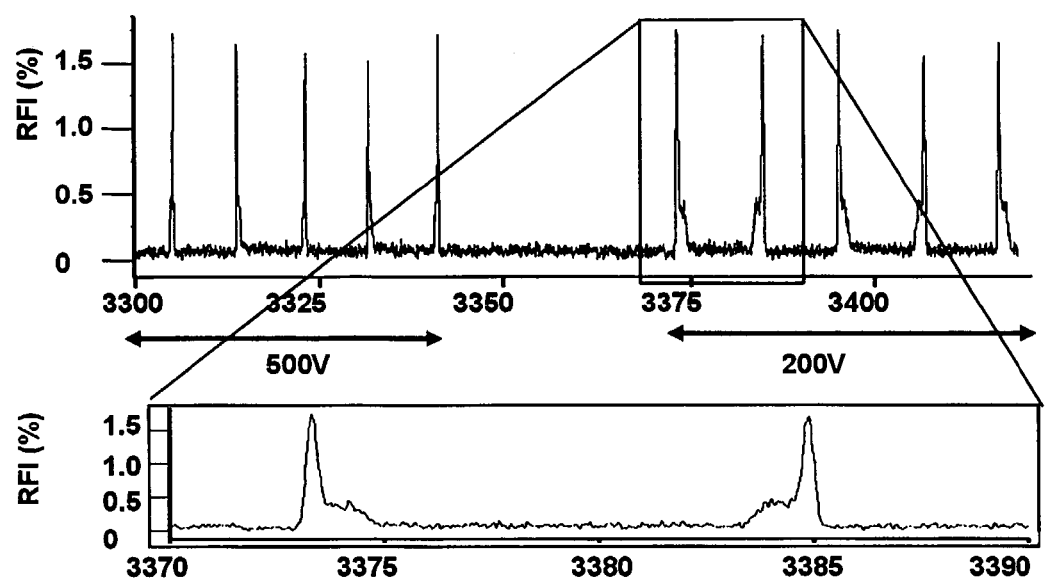

FIG. 19 illustrates the scanning results of a budding yeast cell using a narrow detection window and 2 different scanning speeds. The left five peaks were generated by 500 V, resulting in a faster scanning speed, and the right five peaks were generated by 200V, resulting in a slower scanning speed. The inset shows the 2 mirrored peaks depicting the fluorescent intensities of the mother cell and its bud.

Figure 20:
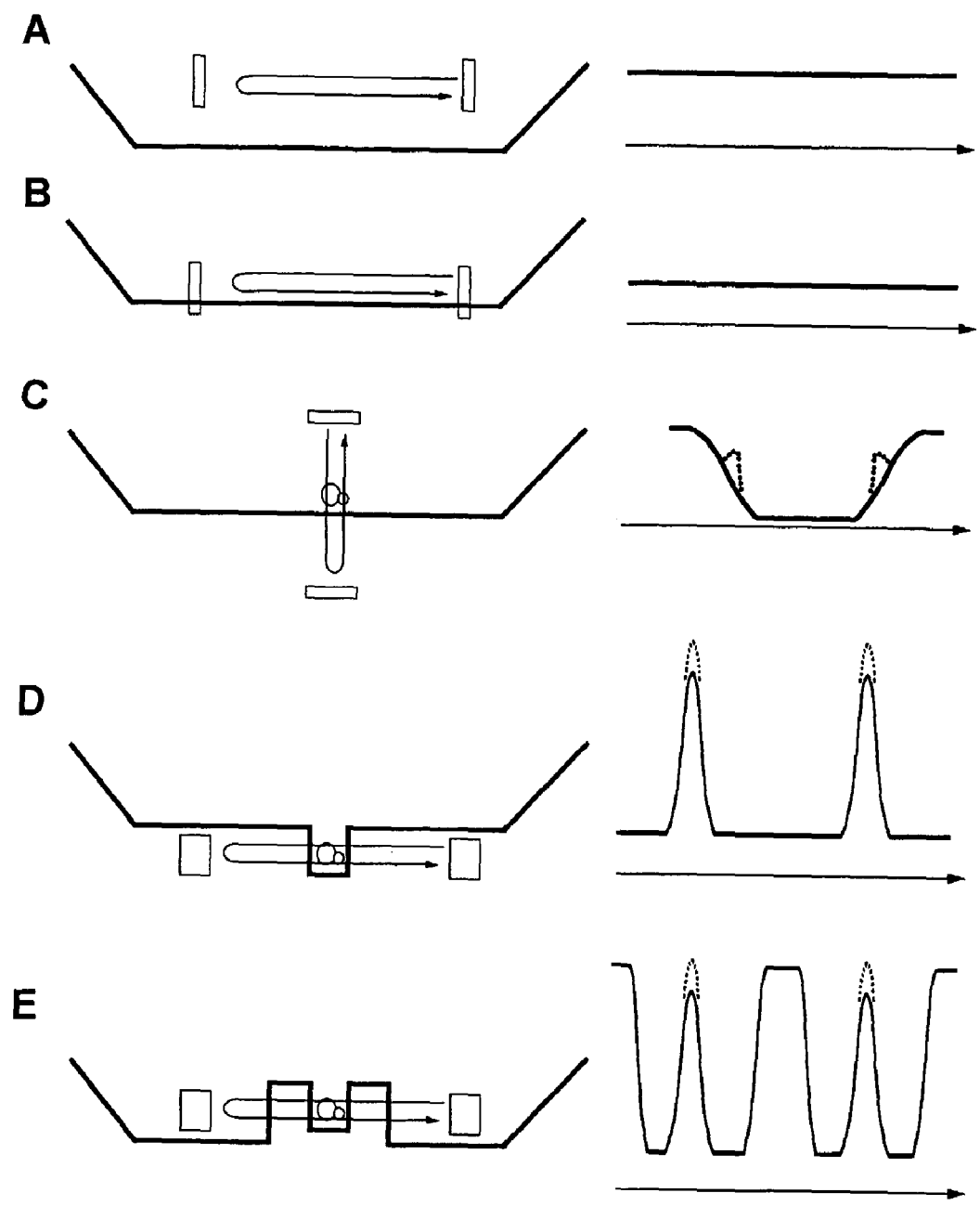

FIG. 20 illustrates an advantage of cell scanning in an open region. The left series of illustrations of A-E show different scanning paths (the arrows indicate the moving detection windows) in different structures. The right series of illustrations of A-E show the expected results from the scanning (the dashed lines in C to E indicate the possible cellular signals).

Figure 21:
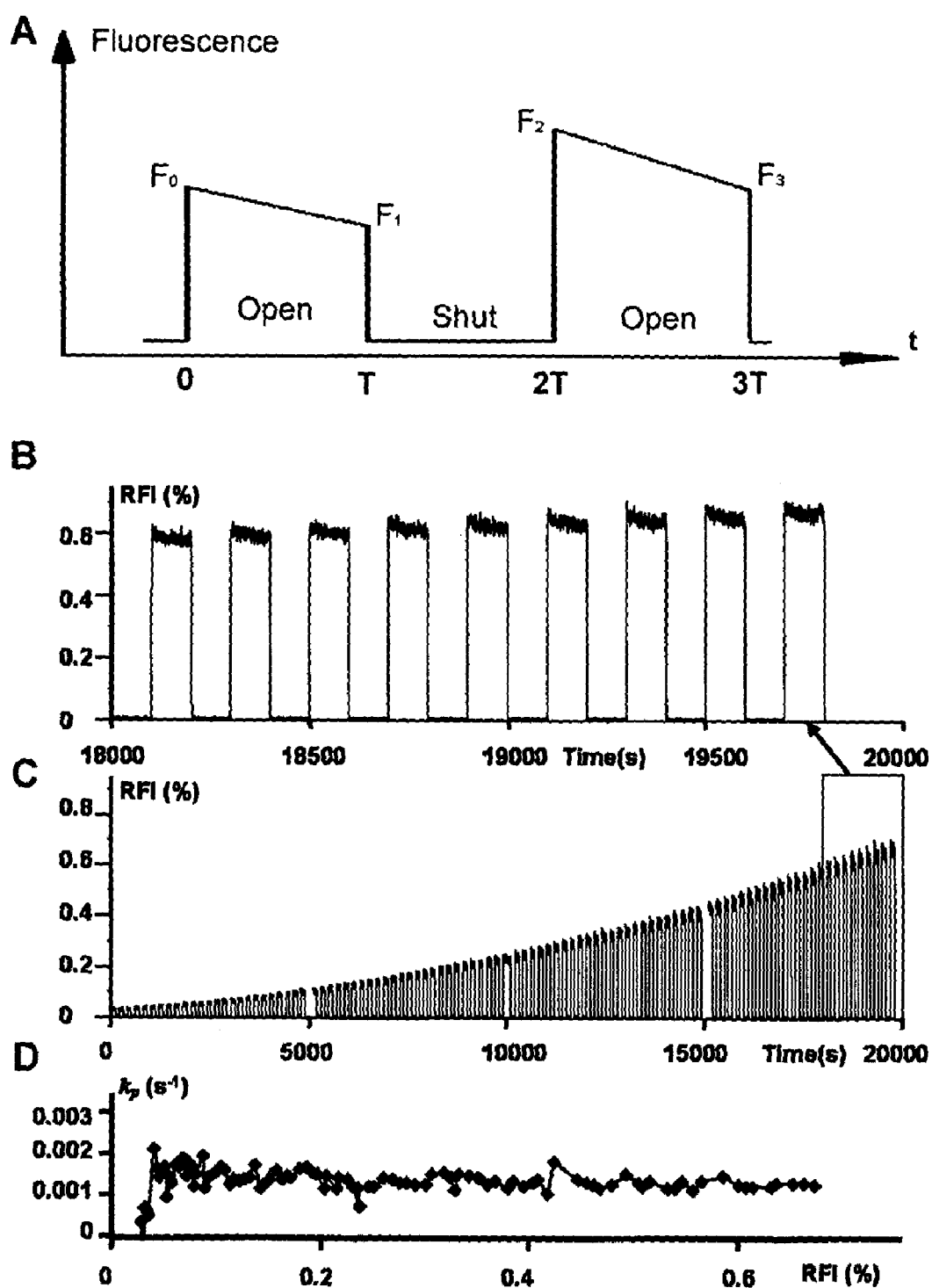

FIG. 21 illustrates the parameters of the photobleaching model to separate FDA hydrolysis (which increases the fluorescent intensity) and the photobleaching effect (which decreases the fluorescent intensity). F0, F1, F2 and F3 are the fluorescence when t=0, T, 2T and 3T, respectively. When 0<t<T and 2T<t<3T, the excitation light is on. When T<t<2T, the excitation light is off. (B) Fluorescent intensity of fluorescein resulted from FDA hydrolysis in G7 without liquid flow. The shutter for the excitation light was opened and shut for an interval of 100 s. (C) the whole experiment which lasted for 20000 s from which the data of (B) is derived. (D) The photobleaching rate constant $k_p$, as determined at each level of relative fluorescent intensity (RFI), is plotted against RFI.

Figure 22:
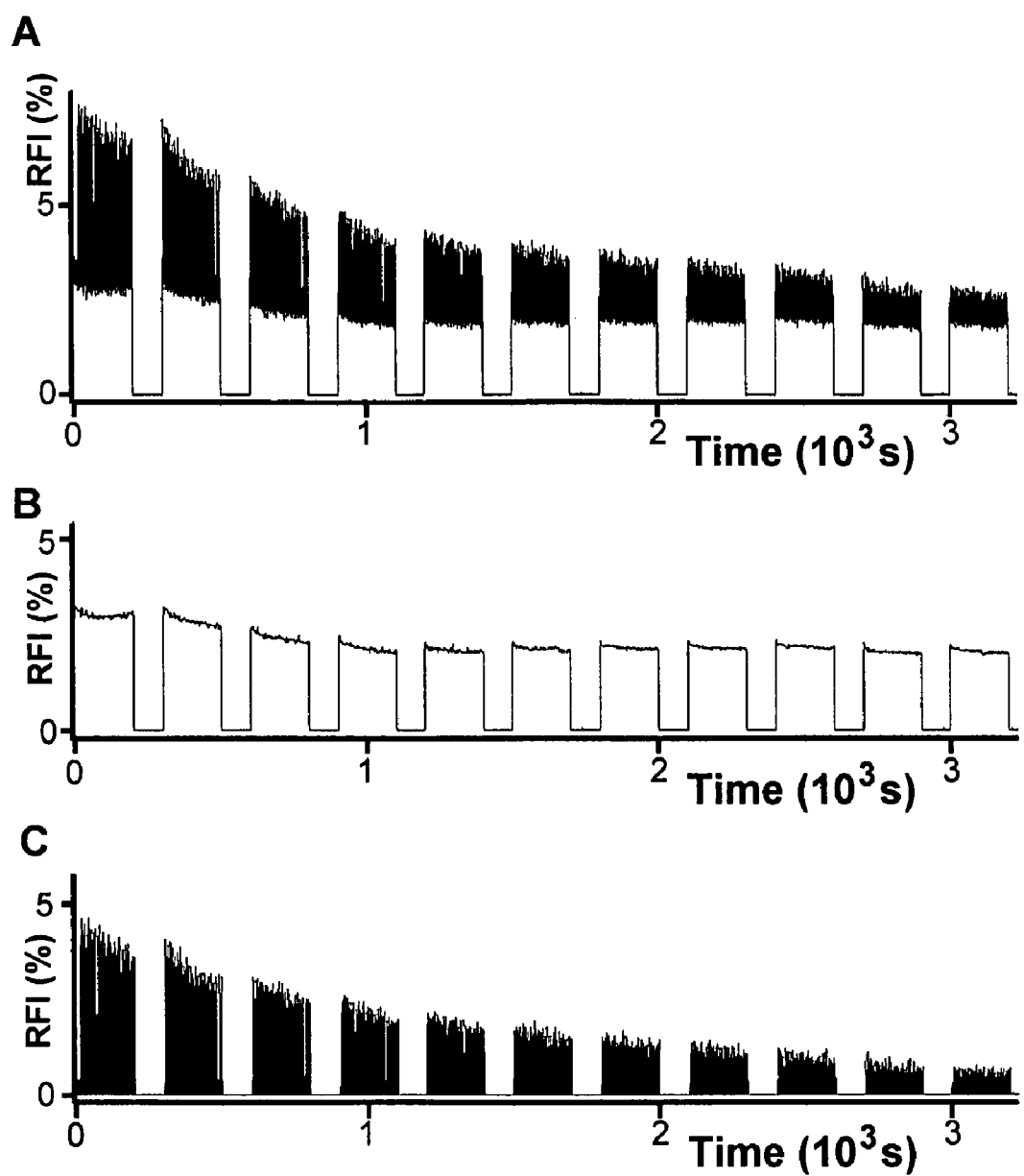

FIG. 22 depicts the fluorescent measurement of a yeast cell embedded on a normal slide: the raw data (A), its separated background (B) and extracted cell fluorescence (C). FDA was used to generate the cellular fluorescence after hydrolysis.

Figure 23:
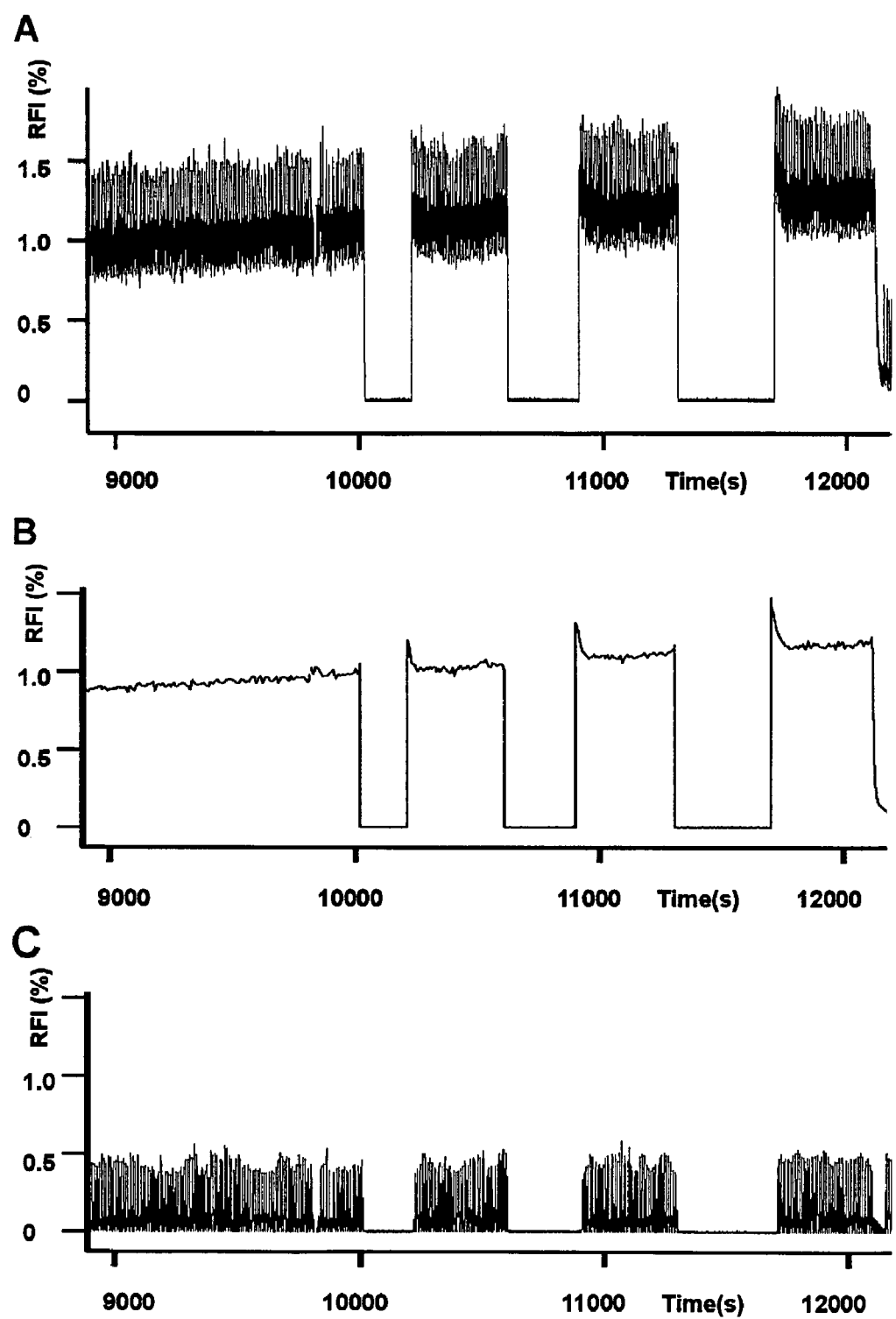

FIG. 23 depicts the fluorescent measurement of a yeast cell under a flow within a microchip: the raw data (A), its separated background (B) and extracted cell fluorescence (C). FDA was used to generate the cellular fluorescence after hydrolysis.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The inventors have developed a microfluidic device which utilizes 3-dimensional flow control. This flow control combines cell balancing capabilities in a first dimension (1-D) as well as cell scanning capabilities in channel dimensions (2-D).

Although the invention is described herein in the context of cells, it will be appreciated by a person skilled in the art that the invention may be used to retain and manipulate other particles, such as beads, viral particles, proteins, protein crystals and nanoparticles.

To balance cells or particles within the microfluidic device, the inventors make use of the downward residual gravitational force of a cell residing on a sloped wall to balance the upward force exerted on the cell by liquid flow through channels or ports in the microfluidic device. The sloped side walls of the microfluidic device can be created, for example, by isotropic etching of a microfluidic device made of materials, such as glass or silicon.

To scan cells and obtain data on biological parameters, the inventors exploit the zero-speed point (ZSP) created by a liquid flow field against a specially shaped particle retention structure in the microfluidic device.

With 3-dimensional flow control, the inventors have successfully carried out cell balancing, cell scanning, measurement of physiological parameters, and observations on a single cell. Yeast cells were chosen for the examples because of their availability and short life cycle (for cell culture). However, the microfluidic device and methods of using the microfluidic device can be used on any type of cell, including prokaryotic cells and eukaryotic cells, such as fungal cells, yeast cells, plant cells and animal cells. As mentioned above, the invention may also be used to study any type of particle, including beads, proteins, protein crystals, nanoparticles and the like.

Furthermore, with the techniques of cell balancing and cell scanning, culturing of a single cell has been accomplished "on-chip." Throughout this application, the term "on-chip" refers to activities which occur within the microfluidic device. Current on-chip culture methods are carried out only in batch mode without keeping track of a single cell, and only for adherent cells[36-41]. The microfluidic device of the invention allows experiments and methods to be carried out with single cells.

3-Dimensional Flow Control

FIG. 1D illustrates an embodiment of the microfluidic device. Referring to FIG. 1D, the microfluidic device 10 consists of a channel defining portion 8 which contains a fluid channel 16, a generally V-shaped particle retention structure 2 spaced apart from channel defining portion 8 which comprises opposed wall portions 4, a central wall portion 6 disposed between opposed wall portions 4, and lateral end portions 18, wherein each opposed wall portion 4 is disposed between central wall portion 6 and one lateral end portion 18. Particle retention structure 2 is generally opposite fluid channel 16. Fluid ports 12 and 14 are defined between channel defining portion 8 and lateral end portions 18. The microfluidic device can comprise more than one fluid channel 16. Alternatively, microfluidic device 10 can also comprise a detection window 30 for detecting cells retained in microfluidic device 10 (see FIG. 1A).

The side walls of opposed wall portions 4 and central wall portion 6 are inwardly sloped. In some embodiments, the inwardly sloped side walls can be inwardly curved, and can be inwardly arcuately sloped (see FIGS. 1A, 1F, and 1G). FIG. 1E is a cross-sectional view of one embodiment of the microfluidic device taken at line S1 as indicated in FIG. 1D. FIG. 1F is a cross-sectional view taken at line S2. FIG. 1G is a magnified view of a portion of FIG. 1F. FIG. 1H is a bisected perspective view of an embodiment of microfluidic device 10.

Angle θ is the angle formed between lateral end portions 18 and opposed wall portions 4. Angle θ can be between 0-180°, such as 135°, or any other suitable angle. For a cell or particle with a diameter of X, the length of central wall portion 6 should be equal to or greater than 2×. The width across fluid port 12 or 14 should be greater than 2×, and can be 4×, for easy particle washing and particle delivery. The depth of the V-shaped particle retention structure, which is the distance from lateral end portions 18 to central wall portion 6, should be 2× or more to keep cells away from fluid which flows across the microfluidic device. In some embodiments, channel 16 can be used to deliver cells or particles to the microfluidic device. In these embodiments, the width of channel 16 can be more than X, which allows cells to be delivered from channel 16 into the microfluidic device. Central wall portion 6 can be flat, or it can comprise one or more grooves, as shown in the embodiments 6A and 6B of the central wall portion in FIG. 1D, to help keep a cell centred over a detection window in the central wall portion. In embodiments where the inwardly sloping side walls of the particle retention structure are arcuately curved, the radius of curvature e of the side walls can be equal to or greater than 2×. However, the inwardly sloping side walls can comprise any curve shape. Moreover, the slope angle of the inwardly sloping side walls can vary or it can be constant.

Referring to FIG. 1B, for cell selection, horizontal liquid flow (from port 12 in this case, although either port 12 or 14 can be used) can carry a group of cells close to the V-shaped particle retention structure. Another flow from channel 16, which is perpendicular to the direction of flow from port 12 or 14, separates the cells and sends a desired cell towards the V-shaped particle retention structure where the detection window is located (FIG. 1C).

For cell balancing and cell scanning, the concept of three-dimensional flow control is exploited (see FIG. 2A). When liquid flows out from channel 16 at a high speed into the more open area of the microfluidic device and towards particle retention structure 2, some fluid will escape sideways and the speed of the flow of the liquid slows. Since particle retention structure 2 is opposite to channel 16, liquid flow will generally follow the contour of particle retention structure 2 and then divide in the centre of particle retention structure 2. Therefore, there exists a zero-speed point (ZSP) in the centre of particle retention structure 2, provided that the two left and right lateral flows are the same. If the two lateral flows are not the same, the ZSP will be displaced. For instance, in FIG. 2B, the ZSP is displaced to the right when the lateral flow toward the left is stronger, due to a higher potential being applied on the right. Stronger lateral flow to the left will shift the ZSP further to the right (see FIG. 2C-D), until the ZSP is no longer within the particle retention structure region or disappears (see FIG. 2E). In the case when there is only lateral flow but no reagent flow (from channel 16), the flow is represented in FIG. 2F. Similarly, situations in which the lateral flow is equal, stronger to the right (due to higher potential applied to the left), or there is no reagent flow are depicted in FIGS. 2G, 2H-J and 2K, respectively. These flows are 2-dimensional in nature. It will be appreciated by persons skilled in the art that flow into channel 16 or lateral ports 12 and 14 can be controlled by electrical, pressure or other suitable means.

Along the third dimension, which is the depth dimension, the liquid flow is not uniform. This situation is depicted in the cross-sectional diagram of FIG. 2A (shown as an inset). Here, even though the flow speed from channel 16 is constant, the flow speed along the sloped side wall of the particle retention structure wall is gradually decreased to zero. Therefore, the ZSP is actually at the upper end of the sloped wall (see the inset of FIG. 2A). This situation is still valid even if the ZSP is displaced sideways due to the differential lateral flows as previously described.

These liquid flows, which are in the channel dimension (lateral and horizontal flows) and the depth dimension (upward flow along the sloped side wall) are therefore 3-dimensional in nature.

For cell scanning, the cell will be stationary and thus retained around the ZSP. Lateral displacement of the ZSP caused by differential lateral flow causes lateral displacement of the cell within the microfluidic device. Periodic lateral displacement of the ZSP therefore causes the cell to be scanned back and forth in the microfluidic device.

Cell balancing is achieved by the balance of forces exerted on a cell (FIG. 2L). First, the cell is pushed upward along the sloped side wall due to the force (f) exerted by the reagent flow. Second, there is resultant force (f") due to the cell's residual gravitational force (g) (after deducting the cell's buoyancy) or sedimentation force and the reaction force (P) acting by the slope on the cell. When the two forces, f and f", are balanced, the cell becomes stationary, and particle retention is achieved.

If the reagent flow is stronger, f increases and the cell is retained at a location higher on the sloped side wall, see FIG. 2M-O. If there is no reagent flow, the cell will not travel up the sloped side wall at all, and will rest on the flat channel bottom, see FIG. 2P.

Accordingly, the strength of the reagent flow is not a great concern. The flow will not crush the cell or flush away the cell because the position of the cell will adjust with the strength of the flow, by moving upwards along the sloped side wall. Furthermore, if the cell lying against the sloped side wall is very near to the top of wall (at the ZSP), the flow speed of the liquid will be very slow compared to that in channel 16. The flow speed will be greater if the cell is farther away from the ZSP. Therefore, a high-speed flow can carry reagents very rapidly and proximately to the cell, and then a low-speed flow will relay those reagents to the cell. All these flow controls can be achieved without any harmful localized force being exerted on the cell. In addition, the position of the cell on the sloped side wall, or the distance of the cell away from the ZSP (FIG. 2M-O), reveals the speed of the flow exerted on the cell, and therefore allows users of the microfluidic device to easily adjust the flow speed by observing the position of the cell within the microfluidic device. In particular, when the cell is scanned back and forth horizontally across the detection window so that signals or biological parameters of cell can be detected, adhesion of the cell, if any, will be minimized, and the cell position will be even more sensitive to assist in adjusting flow rates of liquids from reagent channels or flow ports.

FIG. 3 analyzes the forces balanced on a cell in greater detail. When liquid is further away from the side wall, the liquid flows faster (FIG. 3A). As the liquid approaches the sloped side wall, the liquid follows the shape of the side wall and the flow rate slows. This will cause forces of different directions and strengths to be exerted on a cell of a finite size. FIG. 3B depicts a force $f_\alpha$ exerted at an angle $\alpha$ ($0 \leq \alpha \leq 90°$) to the horizontal. It is balanced by $f'_\alpha$ (or the resultant force of $P_\alpha$ and g). In a special case, a horizontal force $f_H$ (i.e. $\alpha=0$) is balanced by $f'_H$ (or the force resultant $P_H$ and g). For comparison, in the case of a vertical wall (see FIGS. 3C, D), $f_H$ and g are balanced by $P_H$ and $P_V$, respectively, and there is no angular dependence of the liquid force.

The force relationship between, $f_\alpha$, $P_\alpha$ and g is also shown in FIG. 3E. When $\alpha=0$, $f_\alpha$ and $P_\alpha$ attain their maximal values of $f_H$ and $P_H$, respectively, see FIG. 3F. In addition, $f_H$=g tan β, and $P_H$=g|cos β, where β (β<90°) represents the slope angle. For example, if a cell stays at an angle of 45° on the sloped side wall, the reaction force from the wall cannot exceed √2 g, and the flow-induced force cannot exceed g. The reaction force would have a greater limit if β>45°; for instance, if β>60°, the reaction force from the wall cannot exceed 2 g, which is still a small force on the cell. However, users of the microfluidic device can limit the reaction force on the cell by noting the position of the cell on the slope and adjusting liquid flow rates accordingly. On the other hand, if the wall were vertical (FIGS. 3. C, D), the cell could not adjust its position and a strong flow could cause a very high reaction force from the vertical wall ($p_H$).

It is worthwhile to mention that either a sloped side wall or a vertical side wall will give rise to a ZSP due to the splitting of fluid flow. However, only the sloped side wall allows the cell's position to adjust to prevent damage to the cell by a strong flow. The sloped side wall actually serves as a buffer zone. When a cell recedes to a point near the ZSP, the cell can escape from the strong flow. So the sloped side wall is very effective for protecting the cell.

In another embodiment of the invention, the inventors disclose methods of using the microfluidic device of the invention to measure biological parameters of a cell over time, including monitoring changes in biological parameters of a cell in response to various stimuli over time, and culturing a cell in the microfluidic device over one or more life cycles.

It will be understood by a person skilled in the art that the microfluidic device of the invention can also be used with materials other than cells, such as particles, including beads, viral particles, proteins, protein crystals, nanoparticles, and other particles that are capable of being studied with the microfluidic device of the invention. Throughout this application, methods of using the microfluidic device with cells can be applied to particles.

The biological parameters that can be observed and measured include cell morphologies, cell size, growth rate, surface or intracellular biomarkers (e.g. calcium or other minerals or ions, messengers, proteins, carbohydrates, or other suitable biomarkers), influx and efflux of substrates and metabolites, including coloured, chromogenic, fluorescent or radiolabeled substrates and metabolites, reaction to stimuli, reaction to changes in reagent conditions, or any other parameter that would be useful to observe.

In one embodiment, the inventors initiated the influx of a substrate into a single yeast cell, and observed the formation and efflux of a metabolite in response to multiple stimuli over a period of a few hours. In addition, the inventors studied calcium mobilization in a single cell in response to multiple stimuli, in multiple trials.

In another embodiment, using 3-dimensional flow control, a single yeast cell was selected from a group of cells, retained, cultured, and scanned back and forth across a detection window to monitor biological activity within an embodiment of the microfluidic device of the invention.

The microfluidic device of the invention provides a non-disturbing environment to study cells and conduct single-cell experiments. Within the microfluidic device, culture medium can be continually refreshed and cells can freely grow. During experiments, the concentrations of reagents can be changed at any time, and excretion or efflux products are continually flushed away by the flow. Data from single-cell experiments can provide data on real-time changes of the concentration of a metabolic product.

For example, in a conventional solution enzyme model, kinetic parameters of influx, efflux and enzymatic reaction are normally taken as constants. Without single-cell biochemical experiments, it is not possible to test if a cell varies the kinetic parameters or has a strong ability to keep the enzymes under control.

In one of the embodiments of the invention, to study a model of a yeast metabolic process using the microfluidic device of the invention, the inventors selected a cell-permeable fluorogenic substrate, fluorescein diacetate (FDA), which is normally used to determine cell viability[42]. After influx of FDA into a yeast cell, the intracellular enzyme carboxylesterase[43] hydrolyzes FDA to fluorescein, which will then be excreted from the cell (through efflux). Efflux is particularly strong with FDA as compared to other FDA derivatives[45]. Dynamic studies of FDA metabolism in yeast have been performed by flow cytometry[44, 45], but these studies could not completely reveal the complexity of this complex influx-hydrolysis (by esterase)-efflux process.

Accordingly, the inventors introduced FDA to cultured, dormant or treated single yeast cells and obtained kinetic data of the above metabolic process as stimulated by changes in pH and glucose. The inventors achieved these by measuring cellular fluorescent signal due to fluorescein formed in one single yeast cell. These data were then used in a mathematical model to extract the Michaelis-Menten parameters.

In one example discussed below, in response to one type of external stimuli, a yeast cell started to metabolize FDA, and in response to other external stimuli, the yeast cell started to excrete fluorescein. As a result, the inventors identified three modes of cellular control, namely 'self-control', 'lost-control,' and 'death' to describe the metabolic process modes of the cell. The 'self-control' mode describes a cell that can control enzymatic activity. The 'lost-control' mode describes a cell that does not alter enzymatic activity but enzymes may still be working. The 'death' mode describes a cell that does not respond to any changes in its environment. Moreover, these metabolic processes were found to correlate with calcium mobilization.

In another embodiment of the invention, the inventors studied FDA metabolism due to carboxylesterase in response to pH or glucose stimuli. Other enzymes, which act on other substrates, can also be activated by stimuli. In another example, the inventors measured intracellular calcium within a single yeast cell upon various stimuli to study the mobilization of calcium ions.

It will be appreciated by persons skilled in the art that other biological parameters in other cells can also be analyzed through the use of the microfluidic device of the invention. Analysis of other metabolites, in other cells, in response to other stimuli, can also be monitored in the microfluidic device of the invention. On-chip single-cell experiments may be used to elucidate complex biological systems.

EXAMPLES

In examples which are intended to illustrate embodiments of the invention and which are not intended to limit the scope of the invention:

Example 1

Microfluidic Device

FIG. 1 illustrates the design of an embodiment of the microfluidic device and cell selection mechanism. The glass microfluidic device was fabricated through the Protochip Program of Canadian Microelectronic Corporation. Borofloat glass wafers were used to fabricate the channel plate and over plate (16 mm×95 mm). Then, the two glass plates were thermally bonded together to form the finished chip. The layout of one embodiment of the particle retention structure has been depicted in FIG. 1D. In this particular example, the microfluidic device used contained 15 µm deep channels. The side walls of the particle retention structure are inwardly, arcuately sloped in this embodiment. The radius of curvature of the arcuately sloped wide wall should be greater than the diameter of the cell. The central wall portion 6 is normally flat for uniformity in scanning the cell to measure cell parameters. The same microfluidic device was easily washed and reused, and has survived many hours (~200 h) of experiments.

For optical measurements, the microfluidic device was placed on the translation stage of an inverted microscope (Nikon TE 300) with a dual-image module (Nikon) which was coupled to both a CCD video camera (JVC TKC 1380) and a photomultiplier tube (PMT) (Photon Technology Intl, PTI) (FIG. 4). Simultaneous optical observation and fluorescent measurement of the single cell was achieved using this special optical measurement set up. Specifically, red light (>645 nm) was used to observe the cells using the video camera. The motions of any cells were continually displayed on a television monitor and recorded by a video-tape recorder (JVC HR-S7500U). A xenon arc lamp (PTI) was employed to excite the fluorophore. Green fluorescent signals due to intracellular fluorescein formed (520 nm) were not able to reach the camera and could only be detected by the PMT. Fluorescence signals from the PMT were recorded by a computer using the Felix software (PTI). The PMT only recorded the fluorescent signal within the detection window (FIG. 1A). If the yeast cell was within the window, the signal represented the cellular fluorescence plus the fluorescent background. If not, only the fluorescent background was detected.

The 3-dimensional liquid flows could be driven by electric potentials. To create a downward flow of reagents, a high voltage (50-500V) was applied to channel 16, and both ports 12 and 14 were at ground. To create a lateral flow to the right, a high voltage was applied to port 12 with port 14 at ground, and vice versa.

When a high electrolyte buffer was required, e.g. in cell culture experiments, voltage control could not be used, and only fluid potential (by liquid head difference<1 mm) was used. For instance, highly conducting liquid, such as culture medium, was directly introduced in the microfluidic device to the cells (cell 1, 2, 7) used in FIG. 7. By adding, for example, a drop of fluid in only one of the fluid ports, a fluid potential is created and fluid flows through the microfluidic device due to hydrostatic pressure. Alternatively, pumps and valves at fluid ports 12 and 14, and channel 16 may also be used to control liquid flow.

To examine the direction and speed of liquid flow in the microfluidic device, polystyrene beads (6 μm diameter, InSpeck™ Green, Molecular Probes) were used. This bead size was selected because it is similar in size to a yeast cell.

Example 2

Composition of Buffers

In single-cell experiments, the microfluidic device allowed a flow of reagents to be directly delivered to the cell surface. Unlike conventional experiments on normal slides, the inventors could be sure that the reagents or buffers reached the cell at the desired concentration in real-time. FDA stock solution (5 mg/mL in DMSO) was diluted to 12 μM. This concentration of FDA was used because of its limited solubility in aqueous buffers. Two buffers were used for dilution and they were G7 (28.5 mM HEPES, 256 mM D-glucose, pH=7.3) and H4 (285 mM HEPES, pH=4.3). Experiments were performed at room temperature (24° C.) (DMSO: dimethyl sulfoxide; HEPES: N-[2-hydroxyethyl]piperazine-N'-[2-ethanesulfonic acid]).

Example 3

Yeast Strains and Growth Conditions

The yeast (*Sacchomyces cereviase*) strain (wild type, CBY858) was first grown on YPD-agar plates, and were then stored in a refrigerator. Off-chip cell culture was carried out by growing a cell colony aerobically in 2 mL of YPD culture medium (2% glucose, 2% yeast extract and 1% peptone) to the exponential phase ($OD_{600\ nm}$~0.5-1.0). The size of the yeast cell was 2-5 μm.

On-chip cell culture was performed with or without off-chip pre-culture. To initiate off-chip pre-culture, yeast cells were first picked from a colony on an agar plate, and then they were put into 2-ml YPD culture medium for about 7000 s at room temperature (24° C.). Thereafter, the yeast cells in its culture medium were introduced into the microfluidic device. Using 3-dimensional flow control, one budding cell was selected out of a group of cells. Then the inventors provided the cell with more culture medium under a constant flow from the reagent channel 16 to carry out on-chip cell culture. The microfluidic device was maintained at room temperature all the time. The fresh medium flowing from vial c refreshed the cell continually. The cell continued its budding process within the microfluidic device. In the case of direct on-chip culture (i.e. without pre-culture), a cell colony was directly introduced in the microfluidic device. Then a single yeast cell was selected on-chip. Thereafter, YPD culture medium was delivered from the reagent channel to initiate cell growth and budding, as previously described. Removal of the yeast cell wall was achieved by an enzyme, zymolase.

Example 4

Flow Fields in the Microfluidic Device

To image the 3-dimensional flow fields in the microfluidic device, the inventors used both the reagent liquid and polystyrene beads. The inventors used a solution containing FDA to image the flow. After FDA was introduced into the microfluidic device, the FDA flowed out from channel 16 at a high speed and dispersed sideways at a slower speed in the wider portions of the microfluidic device. Movement of the liquid front was recorded by the microscope in the phase-contrast mode (FIG. 5A). It was observed that the speeds of the liquid fronts were not the same in all directions, and the liquid front was not in the shape of a semicircle. Faster lateral flow and slower flow perpendicular to the lateral flow rendered the liquid front to resemble a semi-ellipse. If desired, the flow field lines could be obtained by drawing lines at right angle to the liquid fronts.

As the liquid front did not clearly show how the different flow speeds vary at various locations, the inventors added beads into the reagent channel to indicate the flow field directly (FIG. 5B). Multiple exposures were used in the images to show the paths of beads at their 4 consecutive locations. Therefore, not only can the flow fields be visualized, but also the speeds of the moving beads can be determined. It is demonstrated that the travel speed of the beads slowed as they approached the particle retention device. For instance, in FIG. 5B (0-1 s), a bead rushed out of channel 16 at a speed of about 200 μm/s. Then the bead (as circled) slowed down to a speed of about 60 μm/s (1-2 s). Thereafter, its speed was about 30 m/s near the sloped wall (2-3 s). Finally, the bead was close to the wall and rested on the sloped wall (3-4 s) because the force balance had been achieved. In the meantime, liquid continued to flow from the reagent channel and other beads from the reagent channel demonstrated their speeds as driven by the liquid flow. The immobilization of the bead (as circled) near the ZSP could last for a very long time even in the presence of a fast reagent flow (5-8 s). Since the fluid potential is greater on the left, causing a greater lateral flow to the right, the ZSP near which the bead was retained was displaced to the left side of the particle retention structure. This observation can be compared to FIG. 2H, as discussed above.

Example 5

Selection, Retention, and Scanning of Particles and Cells

Selection, retention and scanning of particles could be easily accomplished, as shown in the multi-exposure images in FIG. 5C. During 0-0.72 s, a bead (as circled) was ejected from channel 16, and moved to the left in the microfluidic device. Meanwhile, a second bead closer to the particle retention structure also moved to the left side of the particle retention structure. When the inventors increased the left fluid potential, both beads turned and moved towards the right (0.72-1.68 s). Meanwhile, the downward reagent flow pushed the first bead further towards the central wall portion of the particle retention structure, though the second bead did not move as much. When the inventors scanned the first bead that they selected, it zigzagged down to the bottom (1.92-2.64 s). The second bead flowed out of the particle retention structure because of the dispersed flow field (2.88-3.60 s) and only the first bead remained (3.84-4.56 s). While the inventors scanned the position of the ZSP in order to retain the bead (as circled), many other beads continually rushed out of the reagent channel, demonstrating the flow directions in the microfluidic device (4.80-25.20 s). These experiments demonstrate that the selection, scanning and retention of the first bead were accomplished by scanning the position of the ZSP. Finally, it should be noted that the bead could be preserved for as long as desired in the particle retention structure (210 s).

Balancing of a bead or cell was also achieved, as shown in FIG. 6. In FIG. 6A, a bead (as circled) was selected in the middle of central wall portion 6 of the particle retention structure (0-1 s). Through reagent flow from channel 16 (shown by the one-second movements of other beads), the retention and scanning of the bead was achieved (7-32 s). FIG. 6B depicts another bead retained at a position closer to the wall outline (0-1 s), which was retained because the reagent flow was stronger, as shown by the longer path traced by the multi-exposure images of the beads. As described in the theory, a stronger reagent flow would cause the particle to be balanced at a higher position on the sloped wall (see FIG. 2M-O), and was therefore seen to be closer to the top of the sloped wall or the wall outline. When the reagent flow was increased even more (4-5 s), the bead started to move up higher on the arc-slope wall, and was balanced at a position even closer to the wall outline (14-15 s). Again, even in the presence of a strong reagent flow, the bead could be retained for a long period of time (24-25 s).

Retention of a fluorescent yeast cell by force balance is depicted in FIG. 6C. First, the cell was pushed upwards and towards the sloped wall close to the wall outline by the reagent flow (0-8 s). Second, the cell was scanned to the right by adjusting the ZSP position using a greater lateral flow from the left to the right (10-16 s). When the reagent flow was increased, the cell appeared to move further up to the wall outline (39-46 s). The scanning of the yeast cell could last for a very long time in the experiment (59-60 s). Occasionally, cell scanning was achieved simply by moving back and forth the microfluidic chip across the detection window, without shifting the ZSP position of the cell. This was achieved by moving the translation stage where the chip was mounted.

Example 7

On-Chip Yeast Cell Culture and Cell-Wall Removal

Based on the 3-dimensional flow control, the cell will not only experience little flow-induced forces, but also experience them uniformly. Accordingly, the inventors consider this flow field as a non-disturbing system for biological cells, which means that the cells could sense little difference between the liquid environment in the microfluidic device and that they normally lived in. Therefore, to take advantage of the non-disturbing system, the inventors cultured a single yeast cell in the microfluidic device using the YPD culture medium. Here, the inventors made use of the short cell cycle of the yeast cell to carry out on-chip cell culture experiments.

After off-chip pre-culture, a single yeast cell (cell 1) was selected using the 3-dimensional flow control. The cell 1 continued its budding process in the microfluidic device, as shown in FIG. 7A. For about 5000 s of on-chip cell culture, cell 1 was larger than its daughter cell. At about 10000 s, the daughter cell began to bud again. At about 15000 s, cell 1 produced its second daughter cell, and additionally cell 1's first daughter cell had borne its own daughter cell. These processes resembled the exponential growth phase in normal off-chip cell culture. At 17039 s, cell 1's daughter and granddaughter flowed out of the microfluidic device, and cell 1 (and its second daughter cell) were selected for subsequent experiments.

In a second on-chip cell culture experiment, a yeast cell colony was directly introduced into the microfluidic device without any off-chip pre-culture. A yeast cell (cell 2) was selected on-chip. With culture medium continually provided from channel 16, a yeast cell started to bud at about 7700 s and continued to grow until 17000 s (FIG. 7B). With this experiment, the inventors were convinced that the yeast cell in the microfluidic device under the 3-dimensional flow control had provided the optimal condition for single-cell culture. These on-chip cell culture experiments were performed at room temperature.

The inventors also attempted on-chip removal of a yeast cell wall by an enzyme (zymolyase). Again, a solution of zymolyase was introduced continually from channel 16 to a selected yeast cell (cell 7). The yeast cell wall was permeabilized and became dark from 480 s to 1200 s (FIG. 7c). Thereafter, the yeast wall collapsed abruptly and it was taken away by the reagent flow. This process lasted for 3.84 s as shown in FIG. 7C (i)-(vii). Cell-wall removal appeared to be necessary for $Ca^{2+}$ fluorescent dye loading in the calcium mobilization experiments.

Example 8

Cell Scannings Signal Detection and Noise Filtering

Normally, fluorescence was monitored continually on a stationary single cell within a fixed detection window. This method was effective when the cellular fluorescence was very strong, and both the noise and the background fluorescence were very low (i.e. high signal-to-noise and signal-to-background ratios). In addition, the background was assumed to be unchanged over the course of the experiments. In single-cell experiments, detection should start before the cell generates strong fluorescent signals. In this case, the low signal-to-background ratio of the cell did not produce any useful information from a stationary cell within a fixed detection window. The situation is worse when background is high.

By using 3-dimensional flow control, scanning a cell back and forth through a fixed detection window generates a series of peaks representing the cell fluorescent signal (FIG. 8A). When the cell was moved out of the detection window, the PMT measured the background fluorescence. When the cell entered the window, the PMT measured the signal together with the background fluorescence. It is shown that the fluorescent intensity of a yeast cell as given by the peak height began to rise due to increased FDA metabolism. Because of the noise, fluorescent intensity was clearly seen only after 75 s (FIG. 8A). Since the data collection rate was 50 Hz and the inventors normally control the peak width from 1s to over 10 s (i.e. 0.1-1 Hz), the inventors performed filtering of noise in the frequency range of 2.5-50 Hz. After filtering the noise in the data represented in FIG. 8A, the results are shown in FIG. 8B. After noise filtering, even the weak cellular signal became very clear, especially during the time of 25-75 s (FIG. 8B). If the measurement had been performed on a stationary cell within a fixed detection window, such low signals would have been missed.

If the detection window was larger than the cell, the peak height represented the total fluorescence of the whole cell regardless of the scanning rate. If the inventors wanted to know the fluorescent distribution of the cell, the inventors could narrow the detection window. This strategy allows differentiation between a larger mother cell and its smaller budding daughter cell. This is illustrated in an experiment involving another yeast cell, as shown in the noise-filtered fluorescent data (FIG. 8C). The high peak came from the mother cell and the shoulder peak was produced by the daughter cell. Scanning the cell back and forth across the detection window generated pairs of mirror peaks.

In some cases, the cell may become adherent to the microchannel bottom in a weak flow, and cannot readily be moved by the cell scanning procedure. In this case, scanning can be performed by moving the detection window, instead of moving the cell. FIG. 18 illustrates different methods of cell scanning. The left series of illustrations of A-D show the different scanning paths (the arrows indicates the moving cells in A and B or the moving detection windows in C and D) in the cell retention structure. The right series of illustrations of A-D show the measurement results. When the detection window is scanned first from right to left, and then from left to right, the double-peaks are obtained (see FIG. 18C), similar to those obtained by cell scanning. Background correction will still be performed, but this is based on the assumption that the background fluorescence near the cell is the same as where the cell lies.

In cell scanning shown in FIG. 18A, the detection window, as depicted as a rectangle, remains stationary, and the cell is scanned, as shown at 2 locations. When the cell passes through the window, strong total fluorescence is detected and a fluorescent peak is generated. When the cell is out of the window, only background is measured. The double peak shape is caused by the yeast mother cell and its small bud, which has a weaker fluorescence than its mother cell. When the bud first enters the window, the small fluorescent peak due to the bud appears at first, followed by a higher peak of the mother cell (see the left double-peak of FIG. 18A). On the other hand, when the cell returns from right to left, the mother cell first enters the window, and the higher peak appears first (see the right double-peak of FIG. 18A). As discussed before; the use of a narrow window during cell scanning provides a means to measure the difference in cellular fluorescence of the yeast cell and its bud. The continual cell scanning process generates a pair of mirror peaks.

When a wider detection window is used, the difference in the fluorescence of the mother cell and its bud cannot be distinguished, thus resulting in only a single peak (FIG. 18B). Since this wider window detects the combined fluorescent intensity from both the mother cell and its bud, the peak height is higher than the double peak obtained from the narrower window. The background is also higher when a larger region is measured using a wider window. However, if the window is too wide, the background increases without the increase in the cellular fluorescence, and there is no advantage in achieving the best signal-to-background ratio. In both cases, background correction is performed by subtracting the background from the total fluorescence.

When using a narrow window for cell scanning, the scanning speed can be adjusted to reveal more details about the difference in the fluorescent intensities of the mother cell and its bud. FIG. 19 shows the results of the cell being scanned at 2 different speeds. For the left set of peaks, a faster scanning speed is obtained because a higher differential voltage (500 V) is applied across the device. These 5 peaks are spaced closer to each other, and the peak widths are smaller, as compared to the right set of peaks which are obtained using a lower differential voltage of 200 V. FIG. 19 inset shows the details about the difference in the fluorescent intensities of the mother cell and its bud, obtainable only at a slower scan speed. These results are obtained from another budding yeast cell, which has a smaller bud, and lower fluorescent intensity, than the cell depicted in FIG. 18.

Advantages of Scanning in an Open Cell Retention Structure

In the scanning procedure, the detection window does not include the walls of the cell retention structure, and this results in a similar background fluorescence over the entire scanning region (FIG. 20A). This procedure is dubbed as equal-background scanning. If the scanning window is moved, for example, to partially include central wall portion 6, the background fluorescence is lower because of less reagent volume detected, although the background is still equal over the scanning region (FIG. 20B). The unchanging background is also essential to detect weak cellular fluorescent signal above the noise of the background. On the other hand, FIG. 20C shows the results of scanning the microfluidic device from top to bottom, in which the background is higher in the reagent region, and lower in the chip region, resulting in a valley-like signal. Any cellular fluorescent signal will only be superimposed on the sloping region of the valley, making it difficult to discern and extract pure cellular fluorescence.

Therefore, an open cell retention structure in the microchip, not only provides the selection and retention of single cells of a wide range of sizes and shapes, but can also provide an open space for equal-background scanning. In addition, reagent switching can take place quickly in the open region to create a homogeneous background around the cell. In contrast, if the cell retention structure is similar in size and shape to the cell, as shown in FIG. 20D or FIG. 20E, the background signal appears as a peak. Also, the background peak occurs at the same location as the cell peak. Therefore, this scanning method would not be useful for background correction with a confined cell retention structure. Moreover, a confined cell retention structure generates complex light scattering, and makes the extraction of the cell fluorescent signal even more difficult. It is also more difficult to distribute reagents to the cell because of the small size of the structure. Any substances excreted by the cell are not easily flushed away in the confined cell retention structure.

Example 9

Background Correction of Detected Signal

In fluorescent measurements, it is feasible to correct for background when the background is measured at the same time as the total signal. The measurement of these 2 parameters has been carried out by cell scanning. Background correction was performed by the following procedure. First, the baseline due to the background fluorescence was determined. Second, the signal peaks were generated by subtraction from the baseline. With the signal peak generated, a peak envelope was created for use in curve fitting to an enzyme model.

In single-cell experiments using different reagents to stimulate the cell, the background fluorescence was not a constant due to the different fluorescent backgrounds of the reagents or buffers. FIGS. 9A and 9B depict the gradual increase in the fluorescent intensity of G7 and H4 buffers, respectively, over 8000 s (or about 2 h). This increase was caused by the slow hydrolysis of FDA in aqueous solutions. By continually switching the buffer between G7 and H4, it was apparent that G7 had a higher fluorescent background (FIG. 9C), presumably due to a greater FDA hydrolysis rate at a higher pH in the G7 buffer.

Using the cell scanning technique, the fluorescent background was recorded as a baseline and the cell fluorescent signal as peaks. In a complex experiment using various reagents at different time points, the fluorescent data appeared to be very strange and were hard to interpret (FIG. 10A). However, the baseline was easily separated (FIG. 10B). After background correction was performed using these baseline data, the peak-only signals were obtained (FIG. 10C). This background correction method enabled the inventors to grasp the real dynamic information from the cell, thus assisting data interpretation.

Furthermore, the baseline provided the inventors with additional information. The inventors could know whether the switching of different buffers, such as between G7 and H4, occurred successfully by examining the baseline (FIG. 10B at 1, 2, 12, 13 ks). Moreover, the inventors shut off the excitation light three times (FIG. 10A-C, 10-12 ks) to determine if photobleaching had any significant effect on cell fluorescence. As discussed below, the fast-decaying baseline showed that the fluorescent background was indeed affected by the photobleaching effect (FIG. 10B, 10-12 ks). Nevertheless, after background correction, the cell showed no apparent decrease in signal (FIG. 10C, 10-12 ks). Finally, the peak envelope (FIG. 10D) was generated, which was significant for curve-fitting to the proposed model of FDA metabolism.

Photobleaching

The inventors determined whether or not photobleaching had an effect on the background. Photobleaching is present when an excitation radiation is used to excite a fluorophore for its emission detection and measurement. Although a Xenon arc lamp was used in these experiments instead of a high-power laser, the photobleaching effect is still present, albeit to a less extent. Since there was no photobleaching when the excitation light shutter was shut off, and photobleaching resumed when the shutter was opened again, this open-shut procedure was used to study the photobleaching effect in the fluorescent measurement system. In this study, the liquid flow was stopped in the microchip, and so there was no replenishment of FDA-containing G7 buffer from the flow. Therefore, the measured fluorescence was dictated only by the processes of fluorescein formation (from FDA hydrolysis) and fluorescein photobleaching as follows.

First, the photobleaching effect is defined as follows, $$\frac{dC}{dt} = -k_p C \quad (1)$$

where C is the concentration of fluorescein and $k_p$ is the photobleaching rate constant.

By integrating equation (1), we have $$\ln\frac{C_T}{C_0} = -k_p T \quad (2)$$

where $C_0$ and $C_T$ are the concentrations of fluorescein when t=0 and t=T, respectively.

Rearranging equation (2), $k_p$ can be obtained as follows, $$k_p = \frac{1}{T}\ln\frac{C_0}{C_T} \quad (3)$$

FIG. 21A is a schematic diagram showing fluorescent intensity when the excitation light is open and shut. Since there is no photobleaching before t=0, $C_0$ is $F_0/m$, where $F_0$ is the initial fluorescent intensity and m represents the instrumental factor relating the measured fluorescent intensity to fluorescein concentration. During 0<t<T, there are both photobleaching and formation of fluorescein from FDA hydrolysis. So the measured fluorescent intensity should be subtracted by an amount due to fluorescein formation, i.e. ($F_2 - F_1$), by assuming that the same extent of fluorescein formation occurred during 0<t<T and T<t<2T. This gives $C_T = [F_1 - (F_2 - F_1)]/m$. Together with $C_0$ and T, $k_p$ can be determined using equation (3).

FIG. 21B shows the changes in the fluorescent background (i.e. no cell) during the open- and shut-cycles (in 100-s intervals) of the shutter for the excitation light. During each open-cycle, the fluorescence decreased due to photobleaching. However, after 100-s of excitation shut-off, the fluorescence became high again due to fluorescein formation, and so the overall fluorescence remained increasing due to on-going FDA hydrolysis. FIG. 21B is actually an expanded region of the experiment over a much longer period, as shown in FIG. 21C. With this data set, more than 100 $k_p$ values were calculated, and plotted in FIG. 21D. This results in an average $k_p$ value of 0.00138±0.00022 $s^{-1}$, as compared to a value of 0.038 $s^{-1}$ reported for free fluorescein in an 0.01 M aqueous solution.[56]

Photobleaching Effect on Cellular Signal

To study the photobleaching effect on the cellular signal, experiments were performed on yeast cells using either a normal slide without liquid flow, or the microchip under a liquid flow.

In the normal slide experiment, there was no liquid flow, and so any free fluorescein was continually photobleached without replenishment. FIG. 22A shows the raw data. After data extraction, FIG. 22B depicts the background, and FIG. 22C shows the extracted cellular signal. It was clear that both the cellular and background fluorescein had photobleaching, as indicated by the gradual drop in fluorescent intensities during each excitation-on period, see FIGS. 22B and 22C, respectively. In FIG. 22B, the fluorescent levels at the start and end of the shut-off period are compared. It is found that there is a slight recovery in the fluorescent level, though the general trend is decreasing. This generally decreasing trend is indicative of the absence of fluorescein replenishment. The recovery after the shut-off period is not obvious in the cellular fluorescence, as shown in FIG. 22C. Moreover, the cellular fluorescence is overwhelmed by the general decreasing trend, possibly caused by the efflux of fluorescein. Since the efflux of fluorescein and its photobleaching cannot be separated in an experiment without flow as conducted in a normal slide, the inventors conducted a microfluidic device flow experiment. It was found as follows that there is no fluorescein efflux and no photobleaching on the cellular fluorescence.

In the microfluidic device experiment, FDA-containing buffer was continually delivered to the cell, and the background level of fluorescein kept increasing because of FDA hydrolysis. The excitation shut-off period was set to 3 values, i.e. 100 s, 200 s, and 300 s, to evaluate the effect of shut-off time on photobleaching. FIG. 23A shows the raw data. After data extraction, FIG. 23B depicts the background, and FIG. 23C shows the extracted cellular signal. It is clear that there is photobleaching of fluorescein in the background, as shown by the sharp drop in the fluorescent intensity (FIG. 23B). Subsequently, the intensity became flat, mainly caused by the replenishment of FDA-containing buffer (and fluorescein) from the flow. After the excitation light was shut off, photobleaching no longer occurred, and the fluorescent intensity recovered to a higher value due to FDA hydrolysis. When the shut-off period is longer, the fluorescent intensity became higher because of more replenishment due to FDA hydrolysis for a longer time.

If the cellular fluorescence had a similar photobleaching effect, the signal should give rise to a characteristic drop during the excitation-on period. But no such drop was observed on the peak envelope after the shut-off period, and the intensity of the series of peaks remained roughly the same (series of peaks in FIG. 23C). This non-photobleaching effect in the yeast cell may be explained by the restricted environment of the fluorescein molecules inside the cell, reducing the photobleaching effect.[55]

Example 10

Single-Cell Experiments on FDA Metabolism

To examine the cells in an embodiment of the microfluidic device, the device was placed on the translation stage of an inverted microscope and simultaneous optical observation and fluorescent measurement were carried out. To carry out fluorescent intensity calibration in the microfluidic device, polystyrene beads (6 μm diameter, InSpeck™ Green, Molecular Probes) were used. Three-dimensional liquid flow control was accomplished by either electric or fluid potential.

With electric potential control, only low-conducting liquids, such as G7, H4 could be delivered to the cells (cell 3, 4, 5). The two buffers were G7 (28.5 mM HEPES, 256 mM D-glucose, pH=7.3) and H4 (285 mM HEPES, pH=4.3). 12 μM FDA was used, where appropriate. With fluid potential (<1 mm) control, highly conducting liquids such as YPD, NaCl, KCl, EDTA could also be used.

Three kinds of yeast cells have been used. The dormant cell was a starved cell taken directly from a cell colony on an agar plate stored in a refrigerator (cells 8, 9, 18, 19, 20, 21, 22, 23, 24). The budding cell was a nourished cell cultured in YPD medium either on-chip (cell 1) or off-chip (cell 3, 4, 5, 6, 14, 15, 16, 17). The spheroplast was a yeast cell with its cell wall removed using an enzyme called zymolase (cell 7, 10, 11, 12, 13), as described previously.

On-chip yeast cell culture and particle retention were carried out for subsequent fluorescent measurement, see FIG. 11. FIG. 11A depicts the particle retention particle retention structure. FIG. 11B-G shows how a yeast cell (cell 1) was selected from a group, and on-chip cell culture of this cell continued. FIG. 11H-K shows how cell 1 was retained and its daughter cells were removed. This cell was subsequently employed for experiments on FDA metabolism (FIG. 12A), and description of this experiment will be given later.

Prior to this experiment, the inventors attempted to introduce FDA (12 μM) in G7 directly to a cultured cell, according to the conventional protocol for testing cell viability[45]. However, the cultured cell (cell 3) produced very weak fluorescent signals (FIG. 12B: 0-1000 s or 0-1 ks). Similar result was observed in another cell (cell 4) (see FIG. 12C, 0-1 ks). Analysis on the weak signal obtained at an earlier stage (FIG. 12D inset, 0-2 ks) showed that the cell had weak responses to pH changes before H4 incubation. On the contrary, the cells stored in the refrigerator (hereafter called the dormant cell) showed strong fluorescent signals. These observations raised several questions. Which cell was viable, the budding cell or dormant cell? When will the metabolism of FDA start in the yeast cell? These questions were not previously asked because of cell heterogeneity in an ensemble. It was the observation from these single-cell experiments that have prompted the inventors to ask these questions.

It is known that the changes of pH and glucose had strong relations to cell growth and metabolism[46,47]. Accordingly, the inventors incubated the cell for 1 ks in a low pH buffer (i.e. H4). It was found that the yeast cells were more sensitive to initiate FDA metabolism and produce strong cell fluorescence (FIG. 12B). In FIG. 12C, FDA metabolism started at 3 ks, and in FIG. 12D, at 2.5 ks. A dramatic increase in fluorescent intensity was also obtained at 18.5 ks in FIG. 12A. Note that background correction was applied in data processing to generate the results, see Example 9 for details. It was concluded that the FDA metabolism was started only after the low-pH incubation.

Another observation was that the efflux of fluorescein spontaneously started without any stimulus at 1.5-2 ks and finished after 4 ks (FIG. 12B). Similar observations of spontaneous fluorescein efflux were also obtained in FIG. 12A (19.2 ks), FIG. 12C (4 ks, 7 ks) and FIG. 12D (4.5 ks). It should be noted that this efflux process could only be observed when the extracellular fluorescein was removed for genuine cellular fluorescein detection, which was very easily achieved in the microfluidic device under a continuous liquid flow.

Furthermore, one single cell could start FDA metabolism again and again by the pH-glucose stimulus (FIG. 12C). The data of FIGS. 12B, C and D were further employed for mathematical modeling, see Example 13.

More experiments showed details of pH and glucose stimulus separately. In FIG. 12E, after on-chip cell selection in YPD medium, experiments on one single yeast cell (cell 6) started. First, FDA in H4 was introduced to the cell. During the period 0-0.3 ks, the cell produced only a small amount of fluorescent signal. However, after this incubation of H4 for 0.3 ks, addition of glucose (G7) resulted in a fluorescent signal increase (0.3 ks-1 ks). Replacement of YPD medium (with no FDA) did not cause any great change on the cell (at 1 ks). Instead, the fluorescent intensity gradually decreased which would be caused by efflux of the fluorescein from the cell (1-2.5 ks). This process caused efflux of fluorescein and resulted in the recovery of the cell for subsequent FDA metabolism studies.

FDA metabolism can be stimulated by the pH stimulus alone. At 2.5 ks, incubation in H4 (with FDA) was performed again (FIG. 12E, 2.5 ks-3.3 ks). This time the fluorescent intensity began to slowly increase. At 3.3 ks, as the low pH was changed to high pH, the cell responded greatly to the sole pH stimulus (3.3 ks-4 ks). To examine the effect of a sole-glucose stimulus, glucose in pH 7.3 (G7) was added at 4 ks (FIG. 12E). It was observed that a small peak appeared on the top of the large fluorescent peak or "mountain", and this demonstrated the cell's response to glucose. This time, the stimulus was caused by glucose alone. Subsequently, the cell spontaneously started its efflux of fluorescein (4.1 ks). The addition of the YPD culture medium without FDA accelerated the efflux of fluorescein (4.25 ks).

The experiment on the same cell (cell 6) continued. At 5.85 ks, a third H4 incubation was performed when H4 with FDA was applied to the cell. During this period, the cell fluorescence remained low. At 6.4 ks, even the glucose in H4 (G4) had no effect on the cell. At 6.7 ks, when the pH of the glucose solution was changed to 7.3, the cell was stimulated again and the fluorescent signal increased continually from 6.7 ks to 7.4 ks. This time, spontaneous efflux was not observed. But the addition of YPD culture medium at 7.4 ks resulted in immediate efflux, even though FDA was in the medium.

After 10 ks (or 3 h) of multiple-stimuli multiple-time experiments on the cell (cell 6), the cell's response became weaker and weaker. Similar experiments conducted on the cell after 10 ks showed low signals until 12 ks. All of these observations revealed that the pH stimulus provided a greater response in initiating the FDA metabolism than the glucose stimulus. However, the presence of glucose was essential to the spontaneous fluorescein efflux, and efflux was stronger in the culture medium, see FIG. 12E at 4.3 ks and 7.4 ks.

In the FDA experiment performed with the on-chip cultured yeast cell (cell 1), the inventors also observed that the efflux started very early and strong (FIG. 12A, 18.5 ks). Note that before the cell's daughter escaped at 16.7 ks, the fluorescent signal included the contributions from the mother cell and its daughter and granddaughter cells. After that, the fluorescent signal only showed the mother cell and its second daughter. So the peak height before 16.7 ks should be reduced.

The inventors have also performed an experiment on a yeast cell after on-chip cell-wall removal. This spheroplast (cell 7) also showed FDA metabolism as soon as FDA (in H7) was added (FIG. 12F). Apparently, the zymolase treatment not only destroyed the cell-wall barrier resulting in more effective influx of FDA, but also created a situation similar to the no-glucose H4 incubation. At 1.3 ks, a glucose stimulus caused immediate efflux. After a while (~0.1 ks), the cell burst, leading to disappearance of fluorescent signals.

Further FDA experiments (FIGS. 12G, H) on dormant yeast cells were performed after experiments on $Ca^{2+}$, discussed below.

Example 11

Single-Cell Experiments On $Ca^{2+}$ Mobilization

Eukaryotic cells can respond (in altering the intracellular $Ca^{2+}$ level) to a wide variety of environmental stress, including changes of pH, and availability of nutrient (e.g. glucose)[48, 49]. Therefore, the effects of these stress factors on the yeast cell can be studied by monitoring mobilization of intracellular $Ca^{2+}$ ions. Intracellular $Ca^{2+}$ is usually measured by fluorescent probes like Indo-1, Fluo-3 or Fluo-4[50]. Loading these probes (as their acetoxylmethyl ester precursors) through the yeast cell wall barrier was slow and difficult, and various methods such as low $pH^{49}$ or electroporation[51] have been attempted.

Calcium mobilization experiments were carried out using a calcium-sensitive dye, Fluo-4. First, Fluo-4 acetoxylmethyl (AM) esters were loaded into the yeast cell either on-chip (cell 10-14) or off-chip (cell 15-24). Formation of Fluo-4 due to hydrolysis of the AM ester within the cell occurred subsequently.

The inventors tried another loading method which involved on-chip cell wall removal using zymolase. After cell wall removal, the yeast cell formed a spheroplast. Then, the loading of the Fluo-4 AM ester into the spheroplast became more effective. Fluo-4 AM ester would then be hydrolyzed by the cellular carboxylesterase to form Fluo-4, which allowed intracellular $Ca^{2+}$ concentration to be detected (FIGS. 13A, B, C, D).

In FIG. 13A, after incubation in H4, the spheroplast (cell 10) was stimulated by G7 with $Ca^{2+}$ (10 mM) and the fluorescent signal due to $Ca^{2+}$ influx or mobilization increased (0.7 ks). The level of fluorescent intensity or intracellular $Ca^{2+}$ was maintained as long as the cell was bathed in external $Ca^{2+}$. At 3.8 ks, removal of external $Ca^{2+}$ caused a slight decrease in fluorescent intensity or intracellular $Ca^{2+}$. At 4.3 ks, switching the buffer to Y (YPD culture medium containing rich nutrients like glucose) caused a sharp decrease in the fluorescent intensity. Based on the observation of spontaneous efflux of the fluorescent FDA metabolite (fluorescein) in the presence of glucose in previous FDA experiments, the inventors believe that this drop in fluorescent intensity due to Fluo-4-$Ca^{2+}$ was caused by the efflux of Fluo-4. More evidence will strengthen this point as described later in this application. Further incubation of H4 (4.5-4.8 ks) and application of G7 with $Ca^{2+}$ at 4.8 ks caused a second rise in fluorescent intensity, albeit low, presumably caused by the continual loss of Fluo-4 due to efflux.

In FIG. 13B, the $Ca^{2+}$ mobilization experiment was repeated. Again, the cell (cell 11) produced fluorescent intensity upon application of G7 with external $Ca^{2+}$ at 0.2 ks. Removal of external $Ca^{2+}$ at 1 ks caused a decrease in fluorescent intensity, in similar manner to FIG. 13A. The decrease continued in either H7 or H4 (1-11.8 ks).

In FIG. 13C, the application of external $Ca^{2+}$ was performed on cell 12 at the same time when H4 was switched to H7 (0.2 ks), instead of switching from H4 to G7 in FIG. 13B. Since the cell produced a fluorescent increase in the absence of glucose, the inventors believe that $Ca^{2+}$ mobilization was caused by the pH stimulus. When switching to G7 (0.8 ks), the cell produced another increase over the high fluorescent intensity, as a response to the glucose stimulus in this time. In the process of fluorescent decrease after removal of external $Ca^{2+}$ at 1.2 ks, application of EDTA (5 mM) in G7 during 1.5-1.7 ks did not produce additional decrease, presumably because the liquid flow had already removed all external $Ca^{2+}$ away from the cell. The re-application of external $Ca^{2+}$ (1.7 ks) did not stimulate another fluorescent increase. Finally, the application of a high concentration of KCl (0.9M) at 1.8 ks caused the fluorescent signal to abruptly drop to a very low level. It is because the spheroplast (without the protection from the yeast cell wall) collapsed in the presence of the hypertonic KCl solution.

The inventors also tried off-chip yeast cell wall removal and on-chip selection for the brightest spheroplast (cell 13) which had already shown cellular fluorescence in G7 containing $Ca^{2+}$ (FIG. 13D). Switching to H4 without $Ca^{2+}$ at 5.2 ks caused a decrease in the fluorescent intensity of the pre-stimulated cell. Since different yeast cells may have different cellular activity, this experiment was performed to choose the cell with the greatest cell activity by on-chip selection of the brightest spheroplast, and then to examine its response to external stimuli. In this manner, the highest signal-to-background ratio of the cell could be obtained, and constant cell scanning was not necessary. However, occasional cell scanning might still be needed if there was any change in background fluorescence due to switching of reagents. Accordingly, such a cell-selection technique was used in subsequent experiments (cells 15-24) to achieve the best signal level. This demonstrates the power of the use of three-dimensional flow control for on-chip single-cell experiments.

It was observed that the increases of $Ca^{2+}$ levels in the spheroplasts (cell 10, 11, 12) in response to pH or glucose change were not very high, as compared with the responses of the brightest spheroplast (cell 13). The inventors suspected the cell membrane of some spheroplasts were compromised in the process of cell-wall removal (even though the dye loaded into the spheroplast should be greater in amount after the cell-wall removal). Therefore, the inventors wanted to try another dye-loading method without the removal of the cell wall. In Fluo-4 AM loading, the concentration of DMSO was usually controlled under 10% (v/v) because of its toxicity[52]. However, the inventors found that the use of a high concentration of Fluo-4 AM in DMSO could generate effective loading into the yeast cells even without cell wall removal as long as a short loading time was used to avoid killing the cells.

In FIG. 13E, on-chip Fluo-4 AM (1 mM) loading was performed on a selected budding cell (cell 14). In this experiment, background correction was not performed to indicate the substantial background fluorescent fluctuations due to the change of reagents (Y, Fluo-4-AM/DMSO, H7, $Ca^{2+}$/H7).

Application of external $Ca^{2+}$ at 0.18 ks produced fluorescence (see also the inset). Since the fluorescent intensity was still not very high, the inventors attributed this to the fact that the loading time could not be controlled to be too short when on-chip loading was used. Therefore, the inventors decided to perform off-chip loading.

Subsequently, the inventors applied off-chip high-concentration Fluo-4 AM loading, followed by $Ca^{2+}$ incubation, and on-chip selection of the brightest cells for $Ca^{2+}$ mobilization experiments (FIG. 13F-O). In FIG. 13F, after short-time (4 s) off-chip dye loading, followed by $Ca^{2+}$ incubation (in G7) and on-chip cell selection, a budding cell (cell 15) already produced very strong fluorescence (0 s). Since the fluorescence was so strong, cell scanning was only performed at the beginning. The background of H4, H7, G7, G4 were very low compared to the signal and they were easy to be corrected (0-1 ks). YPD medium had a higher background, so the inventors used the cell scanning technique again for background correction (after 1 ks). In FIG. 13F, the first stimulus on cell 15 was the pH change from pH 7.3 to pH 4.3 (0.09 ks). This pH stimulus produced a small but obvious increase (see the inset) which could only be explained by $Ca^{2+}$ influx. Afterward, the signal steadily decreased, the inventors re-introduced H7 to the cell as a second stimulus (0.26 ks). This time the budding cell hardly had any response. The subsequent glucose stimulus (0.42 ks) did produce an increase. Up to 13 stimuli were applied to cell 15, including different changes of pH, glucose and even NaCl or KCl. The budding cell had no responses for many stimuli but it produced strong efflux of Fluo-4 in YPD medium which contained glucose (1 ks). Another decrease in fluorescence occurred when H7-E was applied (2 ks) because EDTA (5 mM) could sequester $Ca^{2+}$ and decrease intracellular $Ca^{2+}$.

In FIG. 13G, the budding cell (cell 16) had even less fluorescent change as stimulated by various stimuli, except when external $Ca^{2+}$ was removed at 1.4 ks. In FIG. 3H, the cell (cell 17) was first treated by H4 for 1000s as performed in previous FDA experiments. The cell then strongly responded to the glucose stimulus (from H7 to G7) at 0.18 ks. The second response at 0.52 ks was a pure pH stimulus when pH changed from 4.3 to 7.3 in the presence of glucose (G4-G7). Adding YPD culture medium at 0.9 ks accelerated the efflux of the dye.

In contrast to budding cells, starving dormant cells always had strong $Ca^{2+}$ responses to pH or glucose stimuli as long as there was external $Ca^{2+}$. For instance, FIG. 13I showed that a dormant cell (cell 18) increased its fluorescent intensity as soon as external $Ca^{2+}$ reached the cell (0.4 ks). In the presence of external $Ca^{2+}$, the presence of glucose stimulated a peak due to the $Ca^{2+}$ increase (0.9 ks). Without external $Ca^{2+}$, the pH change could not stimulate a $Ca^{2+}$ peak (1.4 ks).

FIG. 13J showed again that when there was no external $Ca^{2+}$, pH and glucose stimuli could not result in detectable change of fluorescent signal in a dormant cell (cell 19). In FIG. 13K, addition of EDTA to a dormant cell (cell 20) caused removal of $Ca^{2+}$ and fluorescent decrease at 0.2 ks. Note the cell had been treated with $Ca^{2+}$ (in G7) and then selected for experiments. The cell could recover its response to pH/glucose stimuli after external $Ca^{2+}$ was re-applied (0.7 ks).

The inventors performed glucose stimulus two times on another dormant cell (cell 21) (FIG. 13L) at 0.1 ks and 1 ks. The cell responded to the glucose stimulus immediately. After adding YPD medium, fluorescent intensity dropped abruptly because fluo-4 was quickly removed by the cell's efflux. It is concluded that culture medium (YPD) generated quick efflux of Fluo-4, causing the decrease of cellular fluorescent signal. This observation is similar to the efflux of fluorescein in the FDA metabolism experiments, as discussed in Example 10.

More experiments were performed to reveal details about how a cell responded to different stimuli. FIG. 13M showed the responses of a dormant yeast cell (cell 22) to glucose at the same pH 7.3 (0.21 ks), to the pH change (from pH7.3 to 4.3) both in the absence of glucose (0.97 ks) and in the presence of glucose (to the YPD culture medium at 2.1 ks).

FIG. 13N showed the responses of dormant cell (cell 23) to the glucose change at the same pH 7.3 (0.1 ks), and to the YPD culture medium (with glucose) after lengthy incubation in G7 (4 ks).

FIG. 13O showed the responses of another dormant cell (cell 24) to the pH change (no glucose) from pH 7.3 to 4.3 (0.15 ks), to the pH change (no glucose) from 4.3 to 7.3 (0.4 ks), to the glucose change at pH 7.3 (0.7 ks), to the pH change (together with glucose) from 7.3 to 4.3 (1.1 ks), to the pH change from 4.3 to 7.3 in the presence of glucose (1.26 ks), to the YPD culture medium (with glucose) at pH 7.3 (1.75 ks), and to the removal of external $Ca^{2+}$ (2.4 ks to 3.1 ks).

In summary, for budding cells, the $Ca^{2+}$ increase due to the pH and glucose stimuli were very weak. For instance, in FIG. 13F, the fluorescent intensity (proportional to the $Ca^{2+}$ mobilization) changes are 5% for the H7-to-H4 change (or H7-H4), 3% for H7-G7, but undetectable for others. In FIG. 13G, the $Ca^{2+}$ change was undetectable at all.

But after incubation in H4 for 1 ks, the budding cell was starved and could have greater $Ca^{2+}$ increase (FIG. 13H: 24% H7-G7, 6% G7-G4, 13% G4-G7, 3% G7-YPD). For the starved dormant cell, the $Ca^{2+}$ changes were very sensitive to the pH or glucose stimuli (FIG. 13I: 80% H7-G7). Similar observations were obtained in FIG. 13K (22% H7-G7).

It was apparent that $Ca^{2+}$ increase occurred when extracellular $[Ca^{2+}]$ was high (see the scale which represents the concentrations of $Ca^{2+}$ in FIGS. 13I, J, K). In addition, the same stimulus could induce the $Ca^{2+}$ peak more than once on the same cell (FIG. 13L: 12% at 0.1 ks 8% at 0.9 ks for H7-G7).

Multi-stimuli single-cell experiments on the dormant cells (FIGS. 13M, N, O) showed more about the $Ca^{2+}$ increase in response to the pH and glucose stimuli [H7-G7: 25% (cell 22), 69% (cell 23), 14% (cell 24); H7-H4: 19% (cell 22), 27% (cell 24); H4-H7: 8% (cell 24); G7-G4: 6% (cell 24); G4-G7: 29% (cell 24); G7-YPD: 30% (cell 22), 13% (cell 23), 15% (cell 24)]. These experiments show that the changes are reasonable and the cell can respond many times to consecutive multiple stimuli.

In all experiments, (FIG. 13F-O; cells 15-24), the fluorescent intensity had a general decreasing trend. The inventors thought that a cell would always have efflux of the dye to some extent. In the experiment, complex experiments by various stimuli could last over 6 ks (see FIG. 13N) with detectable fluorescent signals.

Apparently, the $Ca^{2+}$ mobilization results showed strong correlation to the FDA metabolism results. In FDA experiments, the dormant cell had the strongest response to the pH or glucose stimuli. The budding cells or cells in the exponential growth phase had the weakest response to pH or glucose stimuli. However, after the 1000 s-incubation in H4, the budding cell became more sensitive to the pH or glucose stimuli.

The experiments of $Ca^{2+}$ showed similar results. The pH and glucose stimuli which started FDA metabolism also caused $Ca^{2+}$ mobilization. Accordingly, the inventors summarized all $Ca^{2+}$ results obtained from FIG. 13 to show the various extents of intracellular $Ca^{2+}$ signal in response to changes in pH, glucose and culture medium for the 3 types of single yeast cells (dormant cell, budding cell and treated budding cell). Since only the relative fluorescent changes (in percentages) were presented, determination of absolute concentration of $Ca^{2+}$ was not needed. As shown in FIG. 14, the percentage changes in $Ca^{2+}$ mobilization are the greatest in dormant cells (up to 25% or above), and the smallest in budding cells (5% or lower). After incubating the budding cells in H4 for 1000 s, the percentage $Ca^{2+}$ changes became greater than those obtained in budding cells without H4 treatment.

In all types of single cells, great $Ca^{2+}$ changes were observed in response to the following stimulation: (1) glucose increase at pH7 (i.e. H7-G7, but not H4-G4); (2) pH change from 4.3 to 7.3 in the presence of glucose (i.e. G4-G7) or from 7.3 to 4.3 without glucose (i.e. H7-H4); (3) the combined stimuli of both changes from pH4.3 to pH 7.3 and from no glucose to glucose (H4-G7). Since the H7-G4 change had only little response, it was not shown in FIG. 14.

After observing that the dormant cell had very strong increase of intracellular $Ca^{2+}$ in response to the glucose stimulus, the inventors then appended two FDA experiments using single dormant cells (FIGS. 12G, H). In FIG. 12G, a dormant cell (cell 8) in YPD culture medium started FDA metabolism as soon as the FDA was applied. Again, the inventors observed spontaneous fluorescein efflux at 1.5 ks, because of the presence of glucose in the YPD medium.

In FIG. 12H, for a dormant cell (cell 9) in H7 (no glucose), FDA metabolism started as soon as FDA was applied. More importantly, a glucose stimulus increased the FDA metabolism to a greater extent, and resulted in a second peak on top of the first fluorescent peak (FIG. 12H, 3.7 ks). Again, spontaneous efflux occurred subsequently at 4.5 ks because of the presence of glucose. This efflux process was accelerated when the buffer was switched to YPD at 6.5 ks.

Example 12

Comparison with Experiments on Normal Slides

For comparison, the inventors have performed some imaging experiments on normal microscope slides. FIGS. 15A, B depict the fluorescent images of yeast cells after FDA addition. In FIG. 15A, most dormant cells could form fluorescein from FDA and become fluorescent. On the other hand, the yeast cells grown to the exponential phase did not show any fluorescence after FDA addition and so the inventors never had a fluorescent image of these budding cells. Only after the incubation of the budding cells in H4 for 1000 s, the treatment of FDA (in G7) to the cells would make most of them become fluorescent due to fluorescein formation (FIG. 15B).

FIGS. 15C, D, E showed the fluorescent images of yeast cells for $Ca^{2+}$ mobilization experiments. Since the cell-permeable Fluo-4 AM in low concentration (10 µM) could not be easily loaded with the yeast cells with cell walls, the inventors applied high-concentration Fluo-4 AM (1 mM) in DMSO for loading, but in very short loading time (4 s) to reduce the toxicity of DMSO. Upon adding external $Ca^{2+}$, some dormant cells (FIG. 15C) and budding cells (FIGS. 15D, E) started to show fluorescence due to Fluo-4-$Ca^{2+}$. For comparison, FIG. 15F represented the image of a fluorescent bead.

In these imaging experiments performed on microscope slides, reagent addition was, and could only be, applied once. However, continuous fluorescent measurements on a single cell with multiple stimuli for dynamic studies have to be performed in the microfluidic device, and only by using the three-dimensional flow control for cell manipulations and reagent delivery.

Example 13

Mathematical Model for FDA Metabolism

So far, the FDA metabolism and calcium mobilization experiments have been qualitative, or semi-quantitative. In order to demonstrate the utility of the single-cell measurement, the inventors developed a mathematical model to describe the kinetics of FDA metabolism. FIG. 16I depicts the schematic diagram of a yeast cell with a daughter bud, showing the relationship between the concentrations of extracellular FDA (A), intracellular FDA (B) and fluorescein (C) as a function of time (t). The kinetic model can be described by several equations. Equation (1) is the material balance of FDA (B) in the cell. Equation (2) is the material balance of fluorescein (C) in the cell. Equations (1) and (2) were derived from first principles as discussed below.

$$\frac{dB}{dt} = \frac{S}{V} k_b (A - B) - \frac{V_m B}{K_m + B} \quad (1)$$

$$\frac{dC}{dt} = \frac{V_m B}{K_m + B} - \frac{S}{V} \frac{V_e C}{K_e + C} \quad (2)$$

The notations are A: extracellular FDA (µM); B: intracellular FDA (µM); C: intracellular fluorescein (µM); S: cell surface area (µm$^2$) and V: cell volume (µm$^3$), as calculated from the diameter (µm) of the cell ($D_1$) and its bud ($D_2$); $k_b$: transport coefficient (µm s$^{-1}$); $V_m$ (µM s$^{-1}$) and $K_m$ (µM): Michaelis-Menten kinetic parameters for the carboxylesterase; $V_e$ (µM µm s$^{-1}$) and $K_e$ (µM): Michaelis-Menten kinetic parameters for the efflux process.

In order to account for the rising part of the fluorescent peak being concave upward, the inventors included an additional equation. More explanations for this equation will be given later.

$$\frac{dV_m}{dt} = k \quad (3)$$

Equation (3) represents the increasing rate of the carboxylesterase activity as indicated by the Michaelis-Menten parameter $V_m$, where k is the rate constant (µM s$^{-2}$).

Derivation for Equation (1): Material Balance of FDA in the Cell

If the total amount of FDA in a cell is $T_B$, then $$T_B = BV \quad (4)$$

where B is the intracellular concentration of FDA and V is the cell volume.

Since V is a constant for the cell in the experiment, then $$\frac{dT_B}{dt} = V \frac{dB}{dt} \quad (5)$$

$dT_B/dt$ can be determined by the influx rate ($F_{in}$) of FDA and its loss due to the hydrolysis rate ($F_h$), $$\frac{dT_B}{dt} = F_{in} - F_h \quad (6)$$

First, $F_{in}$ can be given by Fick's first diffusion law as follows, $$F_{in} = -Sk_D \frac{dB}{dx} \quad (7)$$

where S is the surface area of the cell, which is a constant for the cell in the experiment; $k_D$ is the diffusion coefficient of FDA through the cell membrane, and dB/dx is the concentration gradient of FDA across the cell membrane.

Because of the continuous delivery of buffer and reagent by a liquid flow in the microfluidic chip, the extracellular FDA concentration (A) can be considered as a constant. Assume dB/dx to be a constant value, then it can be calculated from the membrane thickness ($d_m$) to give $$\frac{dB}{dx} = \frac{B-A}{d_m} \quad (8)$$

Combining equations (7) and (8), we have $$F_{in} = Sk_D \frac{A-B}{d_m} \quad (9)$$

where $d_m$, which is a constant for the yeast cell, can be combined with $k_D$ to give $k_b$, and equation (9) becomes $$F_{in} = Sk_b(A-B) \quad (10)$$

Now, $F_h$, which is the enzymatic hydrolysis rate of intracellular FDA, is given by $$F_h = V \frac{V_m B}{K_m + B} \quad (11)$$

It is the Michaelis-Menten kinetic model and $V_m$, and $K_m$ are the usual kinetic parameters.

Combining equations (5), (6), (10) and (11), we obtain equation (1) as follows, $$\frac{V dB}{dt} = Sk_b(A-B) - V\frac{V_m B}{K_m + B} \quad (1)$$

or $$\frac{dB}{dt} = \frac{S}{V}k_b(A-B) - V\frac{V_m B}{K_m + B}$$

Derivation for Equation (2): Material Balance of Fluorescein in the Cell

Intracellular hydrolysis of FDA in the cell increases the amount of fluorescein in the cell, but fluorescein will also be lost due to an efflux process.

In a similar manner to obtain equations (4), (5) and (6), we now have $$V\frac{dC}{dt} = F_h - F_e \quad (12)$$

where C is the intracellular fluorescein concentration, and $F_e$ is the efflux rate of fluorescein after its formation.

$F_e$ can also be described by a second Michaelis-Menten model, $$F_e = S\frac{V_e C}{K_e + C} \quad (13)$$

where $V_e$ and $K_e$ are the usual kinetic parameters; S has been previously defined as the surface area of the cell.

Combining equations (11); (12) and (13), we obtain equation (2) as follows, $$V\frac{dC}{dt} = V\frac{V_m B}{K_m + B} - S\frac{V_e C}{K_e + C_e} \quad (2)$$

or $$\frac{dC}{dt} = \frac{V_m B}{K_m + B} - \frac{S}{V}\frac{V_e C}{K_e + C_e}$$

After numerical calculation by a computer on equations (1), (2) and (3), the model provided the time-course variations of B and C were generated, as given in FIG. 16II. Here, $T_0$, $T_1$ and $T_2$ are the time at which influx, hydrolysis and efflux start, respectively. Using this model, excellent fitting of C to the experimentally measured peak height envelope is obtained (FIG. 16III).

There are four reasons why the inventors developed this model: (1) Even though the external FDA concentration was high, the FDA metabolism in the cell did not always occur. The cell started the FDA metabolism only after incubation at low pH and after some stimuli such as changes in pH or glucose; (2) The rate of fluorescein formation increased with time, as shown by the upward curvature; (3) In constant external FDA concentration, a cell could start the FDA metabolism many times by multiple stimuli; (4) Even though no stimulus was applied to the cell, the cell abruptly started its efflux, i.e. the efflux process was spontaneous.

Usually, the Michaelis-Menten kinetics of enzymes in solutions is studied by the initial-rate method using different substrate concentrations. However, Michaelis-Menten kinetics of enzymes in cells cannot be studied in the same manner because of the additional processes such as substrate influx and product efflux. Therefore, the inventors adopt to study the kinetics by monitoring the progress curve of the internal product concentration over a long period of time.

This new model is different from a previous model developed for cytometry studies[44]. First, the assumptions required for the previous model were no long needed in the on-chip single-cell experiments because (a) The external substrate concentration is indeed time-invariant as the single cell is continually bathed in 12 μM FDA solution in the microfluidic device, (b) External product concentration is indeed much less than the internal product concentration because the efflux product is continually flushed away by the flow in the microfluidic device, (c) Cell-to-cell variation in surface area and volume do not exist in the on-chip experiments performed on a single cell, as compared to many single cells in flow cytometry experiments.

Second, $V_m$ is not a constant because a constant $V_m$ can not explain why the rising part of the peak is concave upwards. The parameter k is included to account for the increasing rate of enzymatic activity, which can be caused by an increasing amount of enzyme. With these considerations, the inventors believe the cell can exert self-control and the inventors adopt 3 different modes in the model to account for the influx, hydrolysis and efflux processes occurring in the single cell. These 3 modes are denoted as the "self-control", "lost control" and "death" modes.

In the self-control mode, when influx is not allowed, $k_b=0$. When influx is allowed, apparently after priming with a low-pH buffer, influx ($T_0$ to $T_1$) occurs in the absence of hydrolysis and efflux, i.e. $k_b>0$, $V_m=0$, and $V_e=0$. During hydrolysis ($T_1$ to $T_2$), there is no influx and efflux, i.e. $k_b=0$, $V_m>0$, and $V_e=0$. Finally, during efflux (after $T_2$), there is no influx and hydrolysis, i.e. $k_b=0$, $V_m=0$, and $V_e>0$. In the lost-control mode, $k_b>0$, $V_m>0$, and $V_e>0$. In the "death" mode, $k_b=0$, $V_m=0$, and $V_e=0$. In this case, the cell appears dead when there is no change in the concentration of cellular fluorescein.

To illustrate the robustness of the model, various sensitivity tests for the parameters: $T_2$-$T_1$, $V_{m0}$, k and $V_e$ (FIG. 16IV-VII) were performed. Note the $V_{m0}$ is the initial value of $V_m$. In FIG. 16IV, the parameter $T_2$-$T_1$ changes, and this affects the starting time of the efflux. In FIG. 16V, the parameter $V_{m0}$ changes, which affects the hydrolysis rate at the beginning. In FIG. 16VI, the parameter k changes, which affects the concavity of the increasing curve. In FIG. 16VII, the parameter $V_e$ changes, which affects the starting rate of the efflux.

Curve-fitting experiments were also carried out for two other single yeast cells under various stimuli, see FIG. 17. In these experiments, the inventors found cellular fluorescence fluctuated many times and there were many maximum peaks. These observations led the inventors to suggest the self-control mode for the FDA metabolism in the yeast cell. Curve fittings were carried out at various time intervals to obtain the various parameters in the 3 model equations depending on whether the cell was in the mode of self-control or lost-control. For instance, for cell 5 (FIG. 17A), during intervals 1-2, 2-3, 3-4, 4-5, the self-control mode was invoked; during intervals 5-8, the lost-control mode was used.

When the cell lost control (i.e. point 5), the inventors observed signal saturation as in the conventional model when there was no change in extracellular FDA. In addition, there was a drop in cellular fluorescence when extracellular FDA was removed (i.e. point 8). Therefore, the conventional model is considered to resemble the lost-control mode in this model. For cell 4 (FIG. 17B), during intervals 11-13, 13-14, 14-15, the self-control mode was invoked; during interval 16-17, the lost-control mode was used. During the self-control mode, the fluorescein efflux was not affected by any change of extracellular FDA (point 12). When the cell lost control (i.e. point 16), signal saturation was again observed. On the other hand, after point 17, it did not respond to any change in buffer and extracellular FDA, and the cellular fluorescent level remained high, so the inventors believed that the cell died.

In this model, the inventors applied three different modes to describe the whole process using the data obtained from single-cell experiments. Therefore, the inventors did not use steady-state calculations. The various parameters of these and other cells, which were obtained from curve fitting, were tabulated in Table 1. Unfortunately, these parameters under similar conditions were not found in the literature for comparison.

TABLE 1

Curve-fitting parameters in the enzymatic model for yeast cell influx/hydrolysis/efflux study. (In all cases, $k_b = 0.04$ µm s$^{-1}$; $K_m = 0.3$ µM; $K_e = 700$ µM)

| Cell | $D_1, D_2$ (µm) | $T_0$ (s) | $T_1 - T_0$ (s) | $T_2 - T_1$ (s) | $V_{m0}$▫ (µM s$^{-1}$) | k# (10$^{-6}$ µM s$^{-2}$) | $V_e$ (µM µm s$^{-1}$) | Mode |
|---|---|---|---|---|---|---|---|---|
| 3 | 5, 5 | 2140 | 70 | 2300 | 0.0012 | 4 | 1 | Self-control |
| 5 | 4, 2 | 208 | 1.6 | 150 | 0.02 | 0 | 0.1 | Self-control |
|  |  | 1030 | 0.3 | 150 | 0.005 | 0 | 0.1 | control |
|  |  | 2026 | 4.5 | 1270 | 0.0018 | 2 | † |  |
|  |  | 3300 | 17 | 1500 | 0.004 | 15 | 1 |  |
|  |  | 5600 | * | * | 0.015 | 0 | 1 | Lost-control |
| 4 | 3.5, 2 | 2560 | 9 | 1250 | 0.002 | 25 | 0.65 | Self-control |
|  |  | 4950 | 8 | 310 | 0.01 | 25 | 0.3 | control |
|  |  | 6590 | 17 | 700 | 0.04 | 0 | 0.8 |  |
|  |  | 8627 | * | * | 0.009 | 0 | 1 | Lost-control |
| ‡ | 5, 5 | 2200 | 100 | 1300 | 0.007 | 4 | 0.6 | Self-control |

When k = 0, this represents constant $V_m$
†$V_e$ and $K_e$ were not needed because cell 5 did not enter the efflux process
*$T_1$ and $T_2$ were not needed in the lost-control mode
‡Another single yeast cell similar to cell 3, which was not described in the text
▫$V_{m0}$ is the initial value of $V_m$ The 3-dimensional flow control concept for single-cell experiments using the microfluidic device of the invention provides a platform for the study of complex biochemical systems in single cells. Experimental results revealed the cellular control on a yeast cell metabolic process using FDA as a model substrate. Further experiments on Ca$^{2+}$ mobilization at the single-cell level suggested correlation with the FDA metabolism experiments. Even though a metabolic process is well understood in the conventional way, experiments with a single cell can reveal further information. The data from the FDA metabolism experiments have been used to fit an enzyme model and obtain relevant parameters.

In this work, the three-dimensional flow control concept has been used to examine the metabolism of a model substrate by an intracellular esterase as well as the mobilization of calcium in a single yeast cell. However, the microfluidic device of the invention can be widely used to study other biochemical processes and to study them on other biological entities, such as mammalian cells, plants cells, bacteria, viruses, and other types of cells.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

REFERENCES

1. P. A. Auroux, D. Lossifidis, D. R. Reyes and A. Manz, Anal. Chem. 2002, 74, 2637-2652.
2. Landers, J. P. Anal. Chem. 2003, 75, 2919.
3. M. A. Northrup, K. F. Jensen and D. J. Harrison eds. Proc. of 7th Intl. Symp. Micro Total Analysis System, October 2003, Squaw Valley, Calif., USA, Transducer Research Foundation, 2003.
4. Wheeler, A. R.; Throndset, W. R.; Whelan, R. J.; Leach, A. M.; Zare, R. N.; Liao, Y. H.; Farrell, K.; Manger, I. D.; Daridon, A. Anal. Chem. 2003, 75, 3581-3586
5. Fu, A. Y.; Spence, C.; Scherer, A.; Arnold, F. H.; Quake, S. R. Nature Biotechnol. 1999, 17, 1109-1111
6. Li, P. C. H.; Harrison, D. J. Anal. Chem. 1997, 69, 1564-1568
7. Voldman, J.; Gray, M. L.; Toner, M.; Schmidt, M. A. Anal. Chem. 74, 2002, 3984-3990
8. Takayama, S.; Mcdonald, J. C.; Ostuni, E.; Liang, M. N.; Kenis, P. J. A.; Smagilov, R. F.; Whiteside, G. M. Proc. Natl. Acad. Sci. 1999, 96, 5545-5548
9. Li, P. C. H.; Camprieu, L.; Cai. J.; Sangar, M.; Labchip 2004, 4, 174-180
10. Schilling, E. A.; Kamholz, A. E.; Yager, P.; Anal. Chem. 2002, 74, 1798-1804
11. Yang, M.; Li, C. W.; Yang, J.; Anal. Chem. 2002, 74, 3991-4001
12. Fu, A. Y.; Spence, C.; Scherer, A.; Arnold, F. H.; Quake, S. R. Nat. Biotechnol. 1999, 17, 1109-1111.
13. Lin, Y. C.; Jen, C. M.; Huang, M. Y.; Wu, C. Y.; Lin, X. Z. Sens. Actuators B. 2001, 79, 137-143.
14. Roper, M. G.; Shackman, J. G.; Dahlgren G. M.; Kennedy, R. T. Anal. Chem. 2003, 75, 4711-4717.
15. McClain, M. A.; Culbertson, C. T.; Jacobson, S. C.; Allbritton, N. L.; Sims, C. E.; Ramsey, R. M. Anal. Chem. 2003, 75, 5646-5655.
16. Sohn, L. L.; Saleh, O. A.; Facer, G. R.; Beavis, A. J.; Allan, R. S.; Notterman, D. A. Proc. Nat. Acad Sci, 2000, 97, 10687-10690.
17. Fu, A. Y.; Chou, H.; Spence, C.; Arnold, F. H.; Quake, S. R. Anal. Chem. 2002, 74, 2451-2457
18. Salimi-Moosavi, H.; Szarka, R.; Andersson, P.; Smith, R.; Harrision, D. J. Proc. Micro Total Analysis Systems '98, Banff, Canada, Oct. 1998, 1998, 69-72
19. Tamaki, E.; Sato, K.; Tokeshi, M.; Sato, K.; Aihara, M.; Kitamori, T. Anal. Chem. 2002, 74, 1560-1564
42. Jones, K. H.; Senft, J. A.; J. Histochem. Cytochem. 1985, 33, 77-79
43. Degrassi, G.; Uotila, L.; Klima, R.; Venturi, V. Appl. Environ. Microbiol. 1999, 65, 3470-3472
44. Wittrup, K. D.; Bailey, J. E. Biotechnol. Bioeng. 1990, 35, 525-532
45. Breeuwer, P.; Drocourt, J. L.; Bunschoten, N.; Zwietering, M. H.; Rombouts, F. M.; Abee, T. Appl. Environ. Microbiol. 1995, 61, 1614-1619
46. Palková, Z. et al. Mol. Biol. Cell. 2002, 13, 3901-3914
47. Ramos, S.; Balbin, M.; Raposo, M.; Valle, E.; Pardo, L. A. J. Gm. Microbiol. 1989, 135, 2413-2422.
48. Denis, V.; Cyert, M. S. J. Cell Biol. 2002, 156, 29-34
49. Halachmi, D.; Eilam, Y.; FEBS Lett. 1989, 256(1-2), 55-61
50. Gee, K. R.; Brown, K. A.; Chen, W-N. U.; Bishop-Stewart, J.; Gray, D.; Johnson, I. Cell Calcium 2000, 27(2), 97-106
51. Iida, H.; Yagawa, Y.; Anraku, Y. J. Biol. Chem. 1990, 256(22), 13391-13399
52. Murata, Y.; Momose, Y.; Hasegawa, M.; Iwahashi, H.; Komatsu, Y. Chem-Bio Informatics Journal 2002, 2(1), 18-31
53. Kell, D. B.; Mendes, P., Technological and Medical Implications of Metabolic Control Analysis (ed. Cornish-Bowden, A. & Cárdenas, M. L. eds.), Dordrecht, Kluwer Academic Publishers, pp. 3-25. (2000)
54. Arias, A. M.; Stewart, A. Cell, 2003, 113, 8-10
55. Song, L.; Varma, C. A. G. O.; Verhoeven, J. W.; Tanke, H. J., Biophy. J., 1996, 70, 2959.
56. L. Song; E. J. Hennink.; I. T. Young; H. J. Tanke, *Biophy. J*, 1995, 68, 2588.

What is claimed is:

1. A microfluidic device comprising:
   a. at least one first channel for introducing a first fluid into the device;
   b. a particle retention structure spaced-apart from the first channel for retaining a particle therein, wherein said particle retention structure is generally V-shaped in a top plan view, the particle retention structure having opposed wall portions and a central wall portion disposed between and joining the opposed wall portions, wherein the particle retention structure is located generally opposite the first channel, and wherein the opposed and central wall portions have sloped side walls extending from an upper portion thereof to a lower portion of said microfluidic device; and
   c. one or more fluid ports disposed between the first channel and the particle retention structure for introducing a second fluid into the microfluidic device, and for allowing one or more of the first and second fluids to flow out of the microfluidic device.

2. A microfluidic device according to claim 1, wherein the sloped side walls are inclined downwardly.

3. A microfluidic device according to claim 1, wherein the sloped side walls are curved.

4. A microfluidic device according to claim 3, wherein the sloped side walls are arcuately curved.

5. A microfluidic device according to claim 4, wherein said arcuately curved side walls have an arc with a radius of curvature which is two or more times the width of the particle to be retained in the microfluidic device.

6. A microfluidic device according to claim 1, wherein the first channel has a width greater than the width of the particle to be retained in the microfluidic device.

7. A microfluidic device according to claim 1, wherein the central wall portion has a width 2 or more times the width of the particle to be retained in the microfluidic device.

8. A microfluidic device according to claim 1, wherein the particle retention structure has a height 2 or more times the width of the particle to be retained in the microfluidic device.

9. A microfluidic device according to claim 1, wherein the width of the one or more fluid ports is 2 or more times the width of the particle to be retained in the microfluidic device.

10. A microfluidic device according to claim 9, wherein the width of the one or more fluid ports is 4 times the width of the particle to be retained in the microfluidic device.

11. A microfluidic device according to claim 1, wherein the opposed wall portions are angled between 0° and 180° relative to lateral end portions of the particle retention structure.

12. A microfluidic device according to claim 11, wherein the opposed wall portions are angled 135° relative to the lateral end portions of the particle retention structure.

13. A microfluidic device according to claim 1, wherein a first fluid is delivered through the first channel, and the first fluid forms a zero speed point against the particle retention structure.

14. A microfluidic device according to claim 13, wherein the zero speed point is laterally shifted by an increase in delivery of the second fluid from one of the one or more fluid ports.

15. A microfluidic device according to claim 13, wherein the zero speed point is laterally shifted by an increase in electric potential or fluid potential in one of the one or more fluid ports.

16. A microfluidic device according to claim 1 further comprising a detection window for detecting a particle retained in the particle retention structure.

17. A microfluidic device according to claim 16, wherein the detection window is located proximate the central wall portion.

18. A microfluidic device according to claim 1, wherein the central wall portion comprises one or more grooves.

19. A microfluidic device according to claim 1, wherein the device comprises two or more particle retention structures.

20. A microfluidic device according to claim 1, wherein the device comprises two or more first channels.

21. A microfluidic device according to claim 1, wherein the device comprises two or more fluid ports located on opposite lateral sides of the particle retention structure.

22. A microfluidic device comprising:
   a. one or more first channels for introducing a first fluid into the device;
   b. a particle retention structure spaced-apart from the first channel for retaining a particle therein, wherein said particle retention structure is generally V-shaped in a top plan view, the particle retention structure having opposed wall portions and a central wall portion disposed between and joining the opposed wall portions, wherein the particle retention structure is located generally opposite the first channel, and wherein the opposed and central wall portions have sloped side walls extending from an upper portion thereof to a lower portion of said microfluidic device; and
   c. fluid ports disposed between the first channel and the particle retention structure for introducing a second fluid into the microfluidic device, and for allowing one or more of the first and second fluids to flow out of the microfluidic device.

23. A method of monitoring, observing, measuring, or recording a biological parameter of a particle comprising:
   introducing a particle into a microfluidic device according to claim 1; and
   monitoring, observing, measuring, or recording a biological parameter of the particle in the microfluidic device.

24. A method according to claim 23, wherein the biological parameter is monitored, observed, measured, or recorded through a detection window in the microfluidic device.

25. A method according to claim 23 further comprising measuring the background levels of the parameter to be monitored, observed, measured, or recorded and subtracting the background levels from the levels of the parameter being monitored, observed, measured, or recorded.

26. A method according to claim 25, wherein measuring the background levels of the parameter comprises adjusting the background levels for photobleaching.

27. A method according to claim 12, wherein the biological parameter is selected from a group consisting of size, morphology, growth rate, biomarkers, influx of a substance, efflux of a substance, reaction of the particle to one or more stimuli, and reaction of the particle to changes in environment of the particle.

28. A method according to claim 27, wherein the substance that is influxed or effluxed is selected from the group consisting of a coloured substance, a chromogenic substance, a fluorescent substance, a fluorescent-labelled substance, and a radio-labeled substance.

29. A method according to claim 23, wherein monitoring, observing, measuring, or recording a biological parameter of the particle comprises measuring a level of fluorescence, colour, or radiation.

30. A method according to claim 23, wherein kinetic or thermodynamic parameters are mathematically extracted from the biological parameter of the particle.

31. A method according to claim 23, wherein the biological parameter is monitored, observed, measured, or recorded through a detection window in the microfluidic device in real-time and over extended periods of time.

32. A method of culturing a cell comprising:
   introducing a cell into a microfluidic device according to claim 1;
   providing the cell in the microfluidic device with a suitable cell culture fluid; and
   growing the cell in the microfluidic device,
   wherein the cell culture fluid is continuously delivered into the microfluidic device to form a zero speed point, and the cell is retained in the zero speed point.

33. A method of treating a particle with a fluid comprising:
   introducing a particle into a microfluidic device according to claim 1,
   delivering a fluid comprising a compound into the microfluidic device; and
   allowing the compound in the fluid to react with, or be adsorbed on, or be absorbed into the particle.

34. A method according to claim 23, wherein the particle is selected from the group consisting of cells, beads, viral particles, proteins, protein crystals, and nanoparticles.

35. A method according to claim 23, wherein the particle is a yeast cell.

36. A method of separating a particle from a group of particles comprising injecting the group of particles into a microfluidic device according to claim 1, continuously injecting fluid into the microfluidic device through the first channel to form a zero speed point, and retaining only one particle in the zero speed point, and allowing other particles in the group of particles to move away from the zero speed point.

37. A method of moving a particle comprising:
   introducing a particle into a microfluidic device according to claim 1;
   subjecting the particle in the microfluidic device to a fluid flow comprising a first fluid from the first channel and a second fluid from the one or more fluid ports;
   isolating the particle in a zero speed point; and
   moving the zero speed point in the microfluidic device by increasing delivery of the second fluid from one of the one or more fluid ports.

38. A method according to claim 23, wherein the particle is a cell.

39. A method according to claim 26, wherein adjusting the background levels for photobleaching comprises adjusting decreased fluorescent levels caused by photobleaching.

* * * * *